(12) United States Patent
Ida et al.

(10) Patent No.: US 11,327,078 B2
(45) Date of Patent: May 10, 2022

(54) MONOCLONAL ANTIBODY AGAINST APOA4, IMMUNOLOGICAL MEASUREMENT METHOD, AND KIT FOR MEASUREMENT

(71) Applicant: Eisai R&D Management Co., Ltd., Tokyo (JP)

(72) Inventors: Yoko Ida, Kyoto (JP); Takashi Obara, Tsukuba (JP); Emiko Yumoto, Tsukuba (JP)

(73) Assignee: Eisai R&D Management Co., Ltd., Tokyo (JP)

( * ) Notice: Subject to any disclaimer, the term of this patent is extended or adjusted under 35 U.S.C. 154(b) by 49 days.

(21) Appl. No.: 16/965,161

(22) PCT Filed: Feb. 25, 2019

(86) PCT No.: PCT/JP2019/007033
§ 371 (c)(1),
(2) Date: Jul. 27, 2020

(87) PCT Pub. No.: WO2019/167874
PCT Pub. Date: Sep. 6, 2019

(65) Prior Publication Data
US 2021/0055300 A1    Feb. 25, 2021

(30) Foreign Application Priority Data
Feb. 27, 2018  (JP) .............................. JP2018-033113

(51) Int. Cl.
*G01N 33/577* (2006.01)
*C07K 16/18* (2006.01)

(52) U.S. Cl.
CPC ........... *G01N 33/577* (2013.01); *C07K 16/18* (2013.01); *G01N 2333/46* (2013.01)

(58) Field of Classification Search
CPC  C07K 16/18; C07K 2317/34; C07K 2317/56; C07K 2317/565; G01N 33/577; G01N 33/92; G01N 2333/46; G01N 2333/47
See application file for complete search history.

(56) References Cited

U.S. PATENT DOCUMENTS

| | | | |
|---|---|---|---|
| 8,067,179 B2* | 11/2011 | Georgiou | G01N 33/566 536/25.4 |
| 9,273,144 B2* | 3/2016 | Andres | C07K 16/40 |
| 9,534,058 B2* | 1/2017 | Stull | A61K 47/6849 |
| 9,777,071 B2* | 10/2017 | Saunders | C12Y 304/13019 |
| 10,113,003 B2* | 10/2018 | Gauthier | A61P 31/00 |
| 10,308,721 B2* | 6/2019 | Williams | A61K 47/6865 |
| 10,428,156 B2* | 10/2019 | Williams | A61P 43/00 |
| 10,513,558 B2* | 12/2019 | Tipton | A61P 35/00 |
| 2004/0234989 A1 | 11/2004 | Kronenberg | |
| 2009/0220958 A1 | 9/2009 | Casellas et al. | |
| 2020/0341014 A1* | 10/2020 | Kimura | G01N 33/53 |

FOREIGN PATENT DOCUMENTS

| | | |
|---|---|---|
| WO | WO 2003/010544 | 2/2003 |
| WO | WO 2007/016716 | 2/2007 |
| WO | WO 2007/057548 | 5/2007 |
| WO | WO-2017159771 A1 * | 9/2017 ........... C12Q 1/6883 |

OTHER PUBLICATIONS

Edwards et al. J. Mol. Biol. 334:103-118. (Year: 2003).*
Lloyd et al. Protein Eng. Design & Select, 22(3):159-168. (Year: 2009).*
Bisgaier et al., "Distribution of apolipoprotein A-IV in human plasma," J. Lipid Res., 1985, 26(1):11-25.
Deng et al., "The structure of dimeric apolipoprotein A-IV and its mechanism of self-association," Structure, 2012, 20(5):767-779.
Dieplinger at al., "Afamin and Apolipoprotein A-IV: Novel Protein Markers for Ovarian Cancer," Cancer Epidemiol Biomarkers prev, 2009, 18(4):1127-1133.
Gordon et al., "Biosynthesis of Human Preapolipoprotein A-IV," J. Biol. Chem., 1984, 259(1):468-474.
Green et al., "Human Apolipoprotein A-IV," J. Clin. Invest., 1980, 65(4):911-919.
Kronenberg et al., "Effect of sample storage on the measurement of lipoprotein[a], apolipoproteins B and A-IV, total and high density lipoprotein cholesterol and triglycerides," J. Lipid Res., 1994, 35(7):1318-1328.
Omori et al., "Impact of serum apolipoprotein A-IV as a marker of cardiovascular disease in maintenance hemodialysis patients," Therapeutic Apheresis and Dialysis, 2010, 14(3):341-348.
PCT International Search Report in International Appln. No. PCT/JP2019/007033, dated May 21, 2019, 8 pages (with English Translation).
PCT Written Opinion in International Appln. No. PCT/JP2019/007033, dated May 21, 2019, 13 pages (with English Translation).
Rosseneu et al., "Quantification of human apolipoprotein A-IV by 'Sandwich'-type enzyme-linked immunosorbent assay," Clinical Chem., 1988, 34(4):739-743.
Stan et al., "Apo A-IV: an update on regulation and physiologic functions," Biochim. Biophys. Acta, 2003, 1631:177-187.
Tokuhara et al., "Specific Expression of Apolipoprotein A-IV in the Follicle-Associated Epithelium of the Small Intestine," Digestive Diseases and Sciences, 2014, 59(11):2682-2692.
Wu et al., "Relative Contributions by Liver and Intestine to Individual Plasma Apolipoproteins in the Rat," J. Biol. Chem., 1979, 254(15):7316-7322.

(Continued)

*Primary Examiner* — Kimberly Ballard
(74) *Attorney, Agent, or Firm* — Fish & Richardson P.C.

(57) ABSTRACT

The present invention provides an anti-APOA4 monoclonal antibody or an antibody fragment thereof capable of accurately measuring apolipoprotein A-IV (APOA4) in a specimen, a measurement method for immunologically measuring APOA4 using the antibody or the antibody fragment thereof, and a kit for measuring APOA4 containing the antibody or the antibody fragment thereof.

31 Claims, 5 Drawing Sheets
Specification includes a Sequence Listing.

(56) References Cited

OTHER PUBLICATIONS

Cheng et al., "Serum ApoA4 levels predicted the progression of renal impairment in T2DM," European Journal of Clinical Investigation, Jun. 1, 2018, 48(6):e12937, 11 pages.

Extended Search Report in European Patent Application No. 19760446.5, dated Oct. 22, 2021, 10 pages.

Zeng et al., "Increased serum protein levels by Yuanshi Shengmai Chenggu Tablet in treatment of avascular osteonecrosis of the femoral head," Nov. 20, 2017, Molecular Medicine Reports, [Retrieved on Oct. 7, 2021], retrieved from: URL www.spandidos-publications.com/mmr/17/2/2121>, pp. 2121-2126, 8 pages.

* cited by examiner

SEQUENCE LISTING

<160> NUMBER OF SEQ ID NOS: 36

<210> SEQ ID NO 1
<211> LENGTH: 1191
<212> TYPE: DNA
<213> ORGANISM: Homo sapiens

<400> SEQUENCE: 1

```
atgttcctga aggccgtggt cctgaccctg gccctggtgg ctgtcgccgg agccagggct      60
gaggtcagtg ctgaccaggt ggccacagtg atgtgggact acttcagcca gctgagcaac     120
aatgccaagg aggccgtgga acatctccag aaatctgaac tcacccagca actcaatgcc     180
ctcttccagg acaaacttgg agaagtgaac acttacgcag gtgacctgca agaagaagctg    240 gtgccctttg ccaccgagct gcatgaacgc ctggccaagg actcggagaa actgaaggag     300
gagattggga aggagctgga ggagctgagg gcccggctgc tgccccatgc caatgaggtg     360
agccagaaga tcggggacaa cctgcgagag cttcagcagc gcctggagcc ctacgcggac     420
cagctgcgca cccaggtcaa cacgcaggcc gagcagctgg ggcgccagct gaccccctac     480
gcacagcgca tggagagagt gctgcgggag aacgccgaca gcctgcaggc ctcgctgagg     540
ccccacgccg acgagctcaa ggccaagatc gaccagaact ggaggagct caagggacgc     600 cttacgccct acgctgacga attcaaagtc aagattgacc agaccgtgga ggagctgcgc     660
cgcagcctgg ctccctatgc tcaggacacg caggagaagc tcaaccacca gcttgagggc     720
ctgaccttcc agatgaagaa gaacgccgag gagctcaagg ccaggatctc ggccagtgcc     780
gaggagctgc ggcagaggct ggcgcccttg gccgaggacg tgcgtggcaa cctgagggc     840 aacaccgagg ggctgcagaa gtcactggca gagctgggtg ggcacctgga ccagcaggtg     900
gaggagttcc gacgccgggt ggagccctac ggggaaaact tcaacaaagc cctggtgcag     960
cagatggaac agctcaggca gaaactgggc ccccatgcgg gggacgtgga aggccacttg    1020
agcttcctgg agaaggacct gagggacaag gtcaactcct tcttcagcac cttcaaggag    1080
aaagagagcc aggacaagac tctctccctc cctgagctgg agcaacagca ggaacagcag    1140
caggagcagc agcaggagca ggtgcagatg ctggcccctt tggagagctg a             1191
```

<210> SEQ ID NO 2
<211> LENGTH: 376
<212> TYPE: PRT
<213> ORGANISM: Homo sapiens

<400> SEQUENCE: 2

Glu Val Ser Ala Asp Gln Val Ala Thr Val Met Trp Asp Tyr Phe Ser

```
            1               5                  10                 15
        Gln Leu Ser Asn Asn Ala Lys Glu Ala Val Glu His Leu Gln Lys Ser
                        20                  25                 30
        Glu Leu Thr Gln Gln Leu Asn Ala Leu Phe Gln Asp Lys Leu Gly Glu
                        35                  40                 45
        Val Asn Thr Tyr Ala Gly Asp Leu Gln Lys Lys Leu Val Pro Phe Ala
                    50                  55                  60
        Thr Glu Leu His Glu Arg Leu Ala Lys Asp Ser Glu Lys Leu Lys Glu
        65                      70                  75                 80
        Glu Ile Gly Lys Glu Leu Glu Glu Leu Arg Ala Arg Leu Leu Pro His
                            85                  90                 95
        Ala Asn Glu Val Ser Gln Lys Ile Gly Asp Asn Leu Arg Glu Leu Gln
                        100                 105                110
        Gln Arg Leu Glu Pro Tyr Ala Asp Gln Leu Arg Thr Gln Val Asn Thr
                        115                 120                125
        Gln Ala Glu Gln Leu Arg Arg Gln Leu Thr Pro Tyr Ala Gln Arg Met
                    130                 135                 140
        Glu Arg Val Leu Arg Glu Asn Ala Asp Ser Leu Gln Ala Ser Leu Arg
        145                     150                 155                160
        Pro His Ala Asp Glu Leu Lys Ala Lys Ile Asp Gln Asn Val Glu Glu
                            165                 170                175
        Leu Lys Gly Arg Leu Thr Pro Tyr Ala Asp Glu Phe Lys Val Lys Ile
                        180                 185                190
        Asp Gln Thr Val Glu Glu Leu Arg Arg Ser Leu Ala Pro Tyr Ala Gln
                        195                 200                205
        Asp Thr Gln Glu Lys Leu Asn His Gln Leu Glu Gly Leu Thr Phe Gln
                    210                 215                 220
        Met Lys Lys Asn Ala Glu Glu Leu Lys Ala Arg Ile Ser Ala Ser Ala
        225                     230                 235                240
        Glu Glu Leu Arg Gln Arg Leu Ala Pro Leu Ala Glu Asp Val Arg Gly
                            245                 250                255
        Asn Leu Arg Gly Asn Thr Glu Gly Leu Gln Lys Ser Leu Ala Glu Leu
                        260                 265                270
        Gly Gly His Leu Asp Gln Gln Val Glu Glu Phe Arg Arg Arg Val Glu
                    275                 280                 285
        Pro Tyr Gly Glu Asn Phe Asn Lys Ala Leu Val Gln Gln Met Glu Gln
                    290                 295                 300
        Leu Arg Gln Lys Leu Gly Pro His Ala Gly Asp Val Glu Gly His Leu
        305                     310                 315                320
        Ser Phe Leu Glu Lys Asp Leu Arg Asp Lys Val Asn Ser Phe Phe Ser
                            325                 330                335
        Thr Phe Lys Glu Lys Glu Ser Gln Asp Lys Thr Leu Ser Leu Pro Glu
                        340                 345                350
        Leu Glu Gln Gln Gln Glu Gln Gln Gln Glu Gln Gln Glu Gln Gln Val
                    355                 360                 365
        Gln Met Leu Ala Pro Leu Glu Ser
        370                 375

<210> SEQ ID NO 3
<211> LENGTH: 5
<212> TYPE: PRT
<213> ORGANISM: Mus musculus

<400> SEQUENCE: 3
```

-continued

```
Gly Tyr Phe Met Ser
1               5

<210> SEQ ID NO 4
<211> LENGTH: 17
<212> TYPE: PRT
<213> ORGANISM: Mus musculus

<400> SEQUENCE: 4

Arg Ile Asn Pro Tyr Asn Gly Asp Thr Phe Tyr Asn Gln Lys Phe Lys
1               5                   10                  15

Gly

<210> SEQ ID NO 5
<211> LENGTH: 7
<212> TYPE: PRT
<213> ORGANISM: Mus musculus

<400> SEQUENCE: 5

Gly Ile Ile Gly Phe Asp Tyr
1               5

<210> SEQ ID NO 6
<211> LENGTH: 5
<212> TYPE: PRT
<213> ORGANISM: Mus musculus

<400> SEQUENCE: 6

Ile Tyr Trp Met Asn
1               5

<210> SEQ ID NO 7
<211> LENGTH: 17
<212> TYPE: PRT
<213> ORGANISM: Mus musculus

<400> SEQUENCE: 7

Gln Ile Tyr Pro Gly Asp Gly Asp Thr Thr Tyr Asn Gly Lys Phe Lys
1               5                   10                  15

Gly

<210> SEQ ID NO 8
<211> LENGTH: 8
<212> TYPE: PRT
<213> ORGANISM: Mus musculus

<400> SEQUENCE: 8

Arg Gly Asp Tyr Val Tyr Asp Tyr
1               5

<210> SEQ ID NO 9
<211> LENGTH: 5
<212> TYPE: PRT
<213> ORGANISM: Mus musculus

<400> SEQUENCE: 9

Ser Tyr Trp Met Ser
1               5

<210> SEQ ID NO 10
<211> LENGTH: 17
<212> TYPE: PRT
<213> ORGANISM: Mus musculus
```

```
<400> SEQUENCE: 10

Gln Val Tyr Pro Gly Asp Gly Asp Thr Tyr Tyr Asn Gly Lys Phe Arg
1               5                   10                  15

Gly

<210> SEQ ID NO 11
<211> LENGTH: 8
<212> TYPE: PRT
<213> ORGANISM: Mus musculus

<400> SEQUENCE: 11

Arg Asp Asn Tyr Cys Leu Asp Phe
1               5

<210> SEQ ID NO 12
<211> LENGTH: 5
<212> TYPE: PRT
<213> ORGANISM: Mus musculus

<400> SEQUENCE: 12

Asn Tyr Trp Leu Asn
1               5

<210> SEQ ID NO 13
<211> LENGTH: 17
<212> TYPE: PRT
<213> ORGANISM: Mus musculus

<400> SEQUENCE: 13

Gln Ile Tyr Pro Gly Asp Gly Asp Thr Asn Tyr Asn Gly Lys Phe Lys
1               5                   10                  15

Gly

<210> SEQ ID NO 14
<211> LENGTH: 8
<212> TYPE: PRT
<213> ORGANISM: Mus musculus

<400> SEQUENCE: 14

Arg Asn Asn Tyr Val Met Asp Tyr
1               5

<210> SEQ ID NO 15
<211> LENGTH: 11
<212> TYPE: PRT
<213> ORGANISM: Mus musculus

<400> SEQUENCE: 15

Arg Pro Ser Glu Asn Ile His Ser Tyr Leu Ala
1               5                   10

<210> SEQ ID NO 16
<211> LENGTH: 7
<212> TYPE: PRT
<213> ORGANISM: Mus musculus

<400> SEQUENCE: 16

Asp Ala Thr Thr Leu Ala Glu
1               5

<210> SEQ ID NO 17
<211> LENGTH: 9
<212> TYPE: PRT
```

<213> ORGANISM: Mus musculus

<400> SEQUENCE: 17

Gln His His Tyr Val Ser Pro Trp Thr
1               5

<210> SEQ ID NO 18
<211> LENGTH: 11
<212> TYPE: PRT
<213> ORGANISM: Mus musculus

<400> SEQUENCE: 18

Lys Ala Ser Gln Asp Val Gly Thr Ala Val Ala
1               5                   10

<210> SEQ ID NO 19
<211> LENGTH: 7
<212> TYPE: PRT
<213> ORGANISM: Mus musculus

<400> SEQUENCE: 19

Trp Ala Ser Thr Arg His Thr
1               5

<210> SEQ ID NO 20
<211> LENGTH: 9
<212> TYPE: PRT
<213> ORGANISM: Mus musculus

<400> SEQUENCE: 20

Gln Gln Tyr Ser Thr Tyr Pro Phe Thr
1               5

<210> SEQ ID NO 21
<211> LENGTH: 11
<212> TYPE: PRT
<213> ORGANISM: Mus musculus

<400> SEQUENCE: 21

Lys Ala Ser Gln Ala Val Gly Ser Ala Val Ala
1               5                   10

<210> SEQ ID NO 22
<211> LENGTH: 7
<212> TYPE: PRT
<213> ORGANISM: Mus musculus

<400> SEQUENCE: 22

Trp Ala Ser Thr Arg His Thr
1               5

<210> SEQ ID NO 23
<211> LENGTH: 9
<212> TYPE: PRT
<213> ORGANISM: Mus musculus

<400> SEQUENCE: 23

Gln Gln Cys Ser Thr Tyr Pro Cys Thr
1               5

<210> SEQ ID NO 24
<211> LENGTH: 11
<212> TYPE: PRT
<213> ORGANISM: Mus musculus

```
<400> SEQUENCE: 24

Lys Ala Ser Gln Asp Val Gly Thr Ser Val Ala
1               5                   10

<210> SEQ ID NO 25
<211> LENGTH: 7
<212> TYPE: PRT
<213> ORGANISM: Mus musculus

<400> SEQUENCE: 25

Trp Ala Ser Ile Arg His Thr
1               5

<210> SEQ ID NO 26
<211> LENGTH: 9
<212> TYPE: PRT
<213> ORGANISM: Mus musculus

<400> SEQUENCE: 26

Gln Gln Tyr Ser Ser Tyr Pro Phe Thr
1               5

<210> SEQ ID NO 27
<211> LENGTH: 116
<212> TYPE: PRT
<213> ORGANISM: Mus musculus

<400> SEQUENCE: 27

Glu Val Gln Leu Gln Gln Ser Gly Pro Glu Leu Val Lys Pro Gly Ala
1               5                   10                  15

Ser Val Lys Ile Ser Cys Lys Ala Ser Gly Tyr Ser Phe Ile Gly Tyr
                20                  25                  30

Phe Met Ser Trp Val Lys Gln Ser His Gly Lys Ser Leu Glu Trp Ile
            35                  40                  45

Gly Arg Ile Asn Pro Tyr Asn Gly Asp Thr Phe Tyr Asn Gln Lys Phe
        50                  55                  60

Lys Gly Lys Ala Thr Leu Thr Val Asp Lys Ser Ser Ser Thr Ala His
65                  70                  75                  80

Met Glu Leu Leu Ser Leu Thr Ser Glu Asp Ser Ala Val Tyr Tyr Cys
                85                  90                  95

Gly Arg Gly Ile Ile Gly Phe Asp Tyr Trp Gly Gln Gly Thr Thr Leu
            100                 105                 110

Thr Val Ser Ser
            115

<210> SEQ ID NO 28
<211> LENGTH: 117
<212> TYPE: PRT
<213> ORGANISM: Mus musculus

<400> SEQUENCE: 28

Gln Val His Leu Gln Gln Ser Gly Ala Glu Leu Val Arg Pro Gly Ser
1               5                   10                  15

Ser Val Lys Ile Ser Cys Lys Ala Ser Gly Tyr Ala Phe Ser Ile Tyr
                20                  25                  30

Trp Met Asn Trp Val Arg Gln Arg Pro Gly Gln Gly Leu Glu Trp Ile
            35                  40                  45

Gly Gln Ile Tyr Pro Gly Asp Gly Asp Thr Thr Tyr Asn Gly Lys Phe
        50                  55                  60
```

Lys Gly Lys Ala Thr Leu Thr Ala Asp Lys Ser Ser Asn Thr Ala Tyr
65                  70                  75                  80

Met His Leu Ser Ser Leu Thr Ser Glu Asp Ser Ala Val Phe Phe Cys
            85                  90                  95

Ala Arg Arg Gly Asp Tyr Val Tyr Asp Tyr Trp Gly Gln Gly Thr Thr
            100                 105                 110

Leu Thr Val Ser Ser
        115

<210> SEQ ID NO 29
<211> LENGTH: 117
<212> TYPE: PRT
<213> ORGANISM: Mus musculus

<400> SEQUENCE: 29

Gln Val Gln Leu Gln Gln Ser Gly Ala Glu Leu Val Lys Pro Gly Ala
1               5                   10                  15

Ser Val Lys Ile Ser Cys Lys Ala Ser Gly Tyr Ala Phe Ser Ser Tyr
            20                  25                  30

Trp Met Ser Trp Val Lys Gln Arg Pro Gly Lys Gly Leu Glu Trp Ile
        35                  40                  45

Gly Gln Val Tyr Pro Gly Asp Gly Asp Thr Tyr Tyr Asn Gly Lys Phe
    50                  55                  60

Arg Gly Lys Ala Thr Leu Thr Ala Asp Lys Ser Ser Ser Thr Ala Tyr
65                  70                  75                  80

Met Gln Leu Ser Ser Leu Thr Ser Glu Asp Ser Ala Val Tyr Phe Cys
            85                  90                  95

Ala Arg Arg Asp Asn Tyr Cys Leu Asp Phe Trp Gly Gln Gly Thr Ser
            100                 105                 110

Leu Thr Val Ser Ser
        115

<210> SEQ ID NO 30
<211> LENGTH: 117
<212> TYPE: PRT
<213> ORGANISM: Mus musculus

<400> SEQUENCE: 30

Gln Val Gln Leu Gln Gln Ser Gly Ala Glu Leu Val Lys Pro Gly Ala
1               5                   10                  15

Ser Val Lys Ile Ser Cys Lys Ala Ser Gly Tyr Thr Phe Ser Asn Tyr
            20                  25                  30

Trp Leu Asn Trp Val Lys Leu Arg Pro Gly Lys Gly Leu Glu Trp Ile
        35                  40                  45

Gly Gln Ile Tyr Pro Gly Asp Gly Asp Thr Asn Tyr Asn Gly Lys Phe
    50                  55                  60

Lys Gly Lys Ala Thr Leu Thr Ala Asp Lys Ser Ser Ser Arg Ala Tyr
65                  70                  75                  80

Met Gln Leu Ser Ser Leu Thr Ser Glu Asp Ser Ala Val Tyr Phe Cys
            85                  90                  95

Ala Arg Arg Asn Asn Tyr Val Met Asp Tyr Trp Gly Gln Gly Thr Ser
            100                 105                 110

Val Thr Val Ser Ser
        115

<210> SEQ ID NO 31
<211> LENGTH: 107

<212> TYPE: PRT
<213> ORGANISM: Mus musculus

<400> SEQUENCE: 31

Asp Ile Gln Met Thr Gln Ser Pro Ala Ser Leu Ser Ala Ser Val Gly
1               5                   10                  15

Glu Thr Val Thr Ile Thr Cys Arg Pro Ser Glu Asn Ile His Ser Tyr
            20                  25                  30

Leu Ala Trp Tyr His Gln Lys Gln Gly Lys Ser Pro Gln Leu Leu Val
        35                  40                  45

Tyr Asp Ala Thr Thr Leu Ala Glu Gly Val Pro Ser Arg Phe Ser Gly
    50                  55                  60

Ser Gly Ser Gly Thr Gln Phe Phe Leu Lys Ile Asn Ser Leu Gln Pro
65                  70                  75                  80

Glu Asp Phe Gly Ser Tyr Tyr Cys Gln His Tyr Val Ser Pro Trp
                85                  90                  95

Thr Phe Gly Gly Gly Thr Lys Leu Glu Ile Lys
            100                 105

<210> SEQ ID NO 32
<211> LENGTH: 107
<212> TYPE: PRT
<213> ORGANISM: Mus musculus

<400> SEQUENCE: 32

Asp Ile Val Met Thr Gln Ser His Lys Leu Met Ser Thr Ser Val Gly
1               5                   10                  15

Asp Arg Val Ser Ile Thr Cys Lys Ala Ser Gln Asp Val Gly Thr Ala
            20                  25                  30

Val Ala Trp Tyr Gln Gln Lys Pro Gly Gln Ser Pro Lys Leu Leu Ile
        35                  40                  45

Tyr Trp Ala Ser Thr Arg His Thr Gly Val Pro Asp Arg Phe Thr Gly
    50                  55                  60

Ser Gly Ser Gly Thr Asp Phe Thr Leu Thr Ile Tyr Asn Val Gln Ser
65                  70                  75                  80

Glu Asp Leu Ala Asp Tyr Phe Cys Gln Gln Tyr Ser Tyr Pro Phe
                85                  90                  95

Thr Phe Gly Ser Gly Thr Lys Leu Glu Ile Lys
            100                 105

<210> SEQ ID NO 33
<211> LENGTH: 107
<212> TYPE: PRT
<213> ORGANISM: Mus musculus

<400> SEQUENCE: 33

Asp Ile Val Met Thr Gln Ser His Lys Phe Met Ser Thr Ser Val Gly
1               5                   10                  15

Asp Arg Val Ser Phe Thr Cys Lys Ala Ser Gln Ala Val Gly Ser Ala
            20                  25                  30

Val Ala Trp Tyr Gln Gln Lys Pro Gly Gln Ser Pro Lys Leu Leu Ile
        35                  40                  45

Tyr Trp Ala Ser Thr Arg His Thr Gly Val Pro Asp Arg Phe Thr Gly
    50                  55                  60

Ser Gly Ser Gly Thr Asp Phe Thr Leu Thr Ile Ser Ser Ala Gln Ser
65                  70                  75                  80

Ala Asp Leu Ala Asp Tyr Phe Cys Gln Gln Cys Ser Thr Tyr Pro Cys

```
                    85                  90                  95
Thr Phe Gly Gly Gly Thr Lys Leu Glu Ile Lys
            100                 105

<210> SEQ ID NO 34
<211> LENGTH: 107
<212> TYPE: PRT
<213> ORGANISM: Mus musculus

<400> SEQUENCE: 34

Asp Ile Val Met Thr Gln Ser His Lys Phe Met Ser Thr Ser Val Gly
1               5                   10                  15

Asp Arg Val Ser Ile Thr Cys Lys Ala Ser Gln Asp Val Gly Thr Ser
            20                  25                  30

Val Ala Trp Tyr Gln Gln Lys Leu Gly Gln Ser Pro Lys Leu Leu Ile
        35                  40                  45

Asn Trp Ala Ser Ile Arg His Thr Gly Val Pro Asp Arg Phe Thr Gly
    50                  55                  60

Ser Gly Ser Gly Thr Asp Phe Ser Leu Thr Ile Ser Asn Val Gln Ser
65                  70                  75                  80

Glu Asp Leu Ala Asp His Phe Cys Gln Gln Tyr Ser Ser Tyr Pro Phe
                85                  90                  95

Thr Phe Gly Ser Gly Thr Lys Leu Glu Ile Lys
            100                 105

<210> SEQ ID NO 35
<211> LENGTH: 20
<212> TYPE: DNA
<213> ORGANISM: Artificial Sequence
<220> FEATURE:
<223> OTHER INFORMATION: mouse IgG heavy chain reverse primer

<400> SEQUENCE: 35
gccagtggat agactgatgg                                           20

<210> SEQ ID NO 36
<211> LENGTH: 21
<212> TYPE: DNA
<213> ORGANISM: Artificial Sequence
<220> FEATURE:
<223> OTHER INFORMATION: mouse Ig light chain reverse primer

<400> SEQUENCE: 36
gatggataca gttggtgcag c                                         21
```

MONOCLONAL ANTIBODY AGAINST APOA4, IMMUNOLOGICAL MEASUREMENT METHOD, AND KIT FOR MEASUREMENT

TECHNICAL FIELD

The present invention relates to a monoclonal antibody that binds to an apolipoprotein A-IV (hereinafter, referred to as APOA4), a method for immunologically measuring APOA4 using the monoclonal antibody, and a kit for measurement that contains the monoclonal antibody.

Priority is claimed on Japanese Patent Application No. 2018-33113, filed Feb. 27, 2018, the content of which is incorporated herein by reference.

BACKGROUND ART

APOA4 is a glycoprotein having a molecular weight of 46 kDa. Most of APOA4 in plasma is considered to be derived from the small intestine (Non-Patent Documents 1 to 3). It is known that APOA4 has many functions, such as an antioxidant effect or an anorectic effect, in addition to being involved in lipid absorption, transport and metabolism (Non-Patent Document 4). In addition, APOA4 is also known as a biomarker in diagnosis of early renal dysfunction, diagnosis of liver disease, and diagnosis of tumor (Patent Documents 1 to 3).

APOA4 is present in blood in free monomers, dimers, or a lipid-bound state binding to chylomicrons or high-density lipoproteins (HDL) (Non-Patent Documents 2 and 5).

In addition, in a solution, the APOA4 monomer and the APOA4 dimer are interconverted by a storage temperature, a concentration, freeze-thaw, and the like, and thus the ratio is not constant (Non-Patent Documents 6).

Several measurement methods of APOA4 by ELISA (Enzyme-Linked Immunosorbent Assay) have been reported. Rosseneu et al. and Kronenberg et al. have reported that human plasma was treated with 4 M urea, and then diluted, and APOA4 in human plasma was measured by ELISA using an anti-APOA4 polyclonal antibody, thereby improving reproducibility (Non-Patent Documents 7 and 8). In addition, it has been reported that APOA4 was measured by ELISA using an anti-APOA4 polyclonal antibody without using a denaturation agent (Patent Documents 1 to 3).

On the other hand, Omori et al. has measured APOA4 in human serum by ELISA using an anti-APOA4 monoclonal antibody without treating serum with a denaturation agent (Non-Patent Document 9).

CITATION LIST

Patent Literature

[Patent Document 1] PCT International Publication No. WO 2003/010544
[Patent Document 2] PCT International Publication No. WO 2007/057548
[Patent Document 3] PCT International Publication No. WO 2007/016716

Non-Patent Literature

[Non-Patent Document 1] Wu, A.-L., et al.: Relative contributions by liver and intestine to individual plasma apolipoproteins in the rat., J. Biol. Chem., 254, 7316-7322, 1979

[Non-Patent Document 2] Green, P. H. R., et al.: Human apolipoprotein A-IV., J. Clin. Invest., 65 (4) 911-919, 1980.
[Non-Patent Document 3] Gordon, J. I., et al.: Biosynthesis of human preapolipoprotein A-IV., J. Biol. Chem., 259, 468-474, 1984.
[Non-Patent Document 4] Stan, S., et al.: Apo A-IV: an update on regulation and physiologic functions., Biochim. Biophys. Acta, 1631, 177-187, 2003
[Non-Patent Document 5] Bisgaier, C. L., et al.: Distribution of apolipoprotein A-IV in human plasma, J. Lipid Res., 26 (1), 11-25, 1985
[Non-Patent Document 6] Deng, X., et al.: The structure of dimeric apolipoprotein A-IV and its mechanism of self-association, Structure, 20 (5), 767-779, 2012
[Non-Patent Document 7] Rosseneu, M., et al.: Quantification of human apolipoprotein A-IV by "Sandwich"-type enzyme-linked immunosorbent assay, Clinical Chem., 34 (4) 739-743, 1988
[Non-Patent Document 8] Kronenberg F., et al.: Effect of sample storage on the measurement of lipoprotein "a", apolipoproteins B and A-IV, total and high density lipoprotein cholesterol and triglycerides, J. Lipid Res., 35 (7), 1318-1328, 1994.
[Non-Patent Document 9] Omori M., et al.: Impact of serum apolipoprotein A-IV as a marker of cardiovascular disease in maintenance hemodialysis patients, Therapeutic Apheresis and Dialysis, 14 (3), 341-348, 2010

DISCLOSURE OF INVENTION

Technical Problem

An object of the present invention provides an anti-APOA4 monoclonal antibody for accurately measuring APOA4 present in various forms such as a monomer and a dimer in a specimen, a measurement method for immunologically measuring APOA4 using the antibody, and a kit for measuring APOA4 that contains the antibody.

Solution to Problem

The present inventors have prepared an anti-APOA4 monoclonal antibody that recognizes and binds to APOA4, screened the anti-APOA4 monoclonal antibody using the APOA4-His monomer that has been once denatured with a denaturation agent, then diluted and refolded as an antigen, found an anti-APOA4 monoclonal antibody that binds to the APOA4 monomer and dimer, and constructed a measurement method for immunologically measuring APOA4 using the antibody and a kit for measuring APOA4 using the antibody.

That is, the present invention is based on the above findings, and includes the following embodiments.

[1] An anti-APOA4 monoclonal antibody or an antibody fragment thereof, each of which specifically binds to an amino acid sequence from an 89th to a 110th amino acid and an amino acid sequence from a 200th to a 224th amino acid of APOA4 including an amino acid sequence represented by SEQ ID NO: 2.

[2] An anti-APOA4 monoclonal antibody or an antibody fragment thereof, each of which specifically binds to APOA4 including an amino acid sequence represented by SEQ ID NO: 2, including:
a heavy chain complementarity determining region (CDR) 1 including an amino acid sequence represented by SEQ ID NO: 3;

a heavy chain CDR2 including an amino acid sequence represented by SEQ ID NO: 4;

a heavy chain CDR3 including an amino acid sequence represented by SEQ ID NO: 5;

a light chain CDR1 including an amino acid sequence represented by SEQ ID NO: 15;

a light chain CDR2 including an amino acid sequence represented by SEQ ID NO: 16; and a light chain CDR3 including an amino acid sequence represented by SEQ ID NO: 17.

[3] The anti-APOA4 monoclonal antibody or the antibody fragment thereof according to [2], including:

a heavy chain variable region including an amino acid sequence represented by SEQ ID NO: 27; and a light chain variable region including an amino acid sequence represented by SEQ ID NO: 31.

[4] The monoclonal antibody or the antibody fragment thereof according to any one of [1] to [3], each of which binds to a monomer and a dimer of APOA4 including the amino acid sequence represented by SEQ ID NO: 2.

[5] An anti-APOA4 monoclonal antibody or an antibody fragment thereof, each of which specifically binds to an amino acid sequence from a 122nd to a 144th amino acid, an amino acid sequence from a 156th to a 177th amino acid, and an amino acid sequence from a 242th to a 252nd amino acid of APOA4 including the amino acid sequence represented by SEQ ID NO: 2.

[6] An anti-APOA4 monoclonal antibody or an antibody fragment thereof, each of which specifically binds to APOA4 including an amino acid sequence represented by SEQ ID NO: 2, including:

a heavy chain CDR1 including an amino acid sequence represented by SEQ ID NO: 6;

a heavy chain CDR2 including an amino acid sequence represented by SEQ ID NO: 7;

a heavy chain CDR3 including an amino acid sequence represented by SEQ ID NO: 8;

a light chain CDR1 including an amino acid sequence represented by SEQ ID NO: 18;

a light chain CDR2 including an amino acid sequence represented by SEQ ID NO: 19; and a light chain CDR3 including an amino acid sequence represented by SEQ ID NO: 20.

[7] The anti-APOA4 monoclonal antibody or the antibody fragment thereof according to [6], including:

a heavy chain variable region including an amino acid sequence represented by SEQ ID NO: 28; and a light chain variable region including an amino acid sequence represented by SEQ ID NO: 32.

[8] The monoclonal antibody or the antibody fragment thereof according to any one of [5] to [7], each of which binds to a monomer and a dimer of APOA4 including an amino acid sequence represented by SEQ ID NO: 2.

[9] An anti-APOA4 monoclonal antibody or an antibody fragment thereof, each of which specifically binds to APOA4 including an amino acid sequence represented by SEQ ID NO: 2, including:

a heavy chain CDR1 including an amino acid sequence represented by SEQ ID NO: 9;

a heavy chain CDR2 including an amino acid sequence represented by SEQ ID NO: 10;

a heavy chain CDR3 including an amino acid sequence represented by SEQ ID NO: 11;

a light chain CDR1 including an amino acid sequence represented by SEQ ID NO: 21;

a light chain CDR2 including an amino acid sequence represented by SEQ ID NO: 22; and a light chain CDR3 including an amino acid sequence represented by SEQ ID NO: 23.

[10] The anti-APOA4 monoclonal antibody or the antibody fragment thereof according to [9], including:

a heavy chain variable region including an amino acid sequence represented by SEQ ID NO: 29; and a light chain variable region including an amino acid sequence represented by SEQ ID NO: 33.

[11] The monoclonal antibody or the antibody fragment thereof according to [9] or [10], each of which binds to a monomer and a dimer of APOA4 including an amino acid sequence represented by SEQ ID NO: 2.

[12] An anti-APOA4 monoclonal antibody or an antibody fragment thereof, each of which specifically binds to APOA4 including an amino acid sequence represented by SEQ ID NO: 2, including:

a heavy chain CDR1 including an amino acid sequence represented by SEQ ID NO: 12;

a heavy chain CDR2 including an amino acid sequence represented by SEQ ID NO: 13;

a heavy chain CDR3 including an amino acid sequence represented by SEQ ID NO: 14;

a light chain CDR1 including an amino acid sequence represented by SEQ ID NO: 24;

a light chain CDR2 including an amino acid sequence represented by SEQ ID NO: 25; and a light chain CDR3 including an amino acid sequence represented by SEQ ID NO: 26.

[13] The anti-APOA4 monoclonal antibody or the antibody fragment thereof according to [12], including:

a heavy chain variable region including an amino acid sequence represented by SEQ ID NO: 30; and a light chain variable region including an amino acid sequence represented by SEQ ID NO: 34.

[14] The monoclonal antibody or the antibody fragment thereof according to [12] or [13], each of which binds to a monomer and a dimer of APOA4 including an amino acid sequence represented by SEQ ID NO: 2.

[15] A measurement method for immunologically measuring APOA4 in a specimen, the method including:

binding APOA4 including the amino acid sequence represented by SEQ ID NO: 2 in the specimen to a capture antibody which specifically binds to the APOA4, adding a labeled detection antibody in which a label is bound to a detection antibody that specifically binds to the APOA4 to form an immune complex consisting of the APOA4, the capture antibody and the labeled detection antibody, and measuring an amount of label in the formed immune complex, in which the capture antibody and the detection antibody are selected from the anti-APOA4 monoclonal antibody or the antibody fragment thereof according to any one of [1] to [14], and the capture antibody and the detection antibody are different from each other.

[16] The measurement method according to [15], in which the capture antibody is the anti-APOA4 monoclonal antibody or the antibody fragment thereof according to any one of [1] to [4].

[17] The measurement method according to [15] or [16], in which the detection antibody is the anti-APOA4 monoclonal antibody or the antibody fragment thereof according to any one of [5] to [14].

[18] The measurement method according to any one of [15] to [17], in which the capture antibody is the anti-APOA4 monoclonal antibody or the antibody fragment thereof according to any one of [1] to [4], and the detection antibody is the anti-APOA4 monoclonal antibody or the antibody fragment thereof according to any one of [5] to [8].

[19] The measurement method according to any one of [15] to [17], in which the capture antibody is the anti-APOA4 monoclonal antibody or the antibody fragment thereof according to any one of [1] to [4], and the detection antibody is the anti-APOA4 monoclonal antibody or the antibody fragment thereof according to any one of [9] to [11].

[20] The measurement method according to any one of [15] to [17], in which the capture antibody is the anti-APOA4 monoclonal antibody or the antibody fragment thereof according to any one of [1] to [4], and the detection antibody is the anti-APOA4 monoclonal antibody or the antibody fragment thereof according to any one of [12] to [14].

[21] The measurement method according to any one of [15] to [20], in which the label is an enzyme.

[22] The measurement method according to any one of [15] to [21], in which the capture antibody is immobilized on a solid support.

[23] The measurement method according to any one of [15] to [22], in which the specimen is selected from the group consisting of blood, a lymphatic fluid, a tissue fluid, and a body cavity fluid.

[24] The measurement method according to any one of [15] to [23], in which the specimen is blood.

[25] The measurement method according to [24], in which the blood is whole blood, plasma or serum.

[26] A kit for measuring APOA4 in a specimen, including:
a capture antibody that specifically binds to APOA4 including an amino acid sequence represented by SEQ ID NO: 2; and
a labeled detection antibody in which a label is bound to a detection antibody that specifically binds to the APOA4,
in which the capture antibody and the detection antibody are selected from the anti-APOA4 monoclonal antibody or the antibody fragment thereof according to any one of [1] to [14], and the capture antibody and the detection antibody are different from each other.

[27] The kit according to [26], in which the capture antibody is the anti-APOA4 monoclonal antibody or the antibody fragment thereof according to any one of [1] to [4].

[28] The kit according to [26] or [27], in which the detection antibody is the anti-APOA4 monoclonal antibody or the antibody fragment thereof according to any one of [5] to [14].

[29] The kit according to any one of [26] to [28], in which the capture antibody is the anti-APOA4 monoclonal antibody or the antibody fragment thereof according to any one of [1] to [4], and the detection antibody is the anti-APOA4 monoclonal antibody or the antibody fragment thereof according to any one of [5] to [8].

[30] The kit according to any one of [26] to [28], in which the capture antibody is the anti-APOA4 monoclonal antibody or the antibody fragment thereof according to any one of [1] to [4], and the detection antibody is the anti-APOA4 monoclonal antibody or the antibody fragment thereof according to any one of [9] to [11].

[31] The kit according to any one of [26] to [28], in which the capture antibody is the anti-APOA4 monoclonal antibody or the antibody fragment thereof according to any one of [1] to [4], and the detection antibody is the anti-APOA4 monoclonal antibody or the antibody fragment thereof according to any one of [12] to [14].

[32] The kit according to any one of [26] to [31], in which the label is an enzyme.

[33] The kit according to any one of [26] to [32], in which the capture antibody is immobilized on a solid support.

Advantageous Effects of Invention

According to the present invention, there are provided an anti-APOA4 monoclonal antibody capable of accurately measuring APOA4 in a specimen, a measurement method for immunologically measuring APOA4 using the antibody, and a kit for measurement of APOA4 containing the antibody are provided.

BEST MODE FOR CARRYING OUT THE INVENTION

Figure 1:
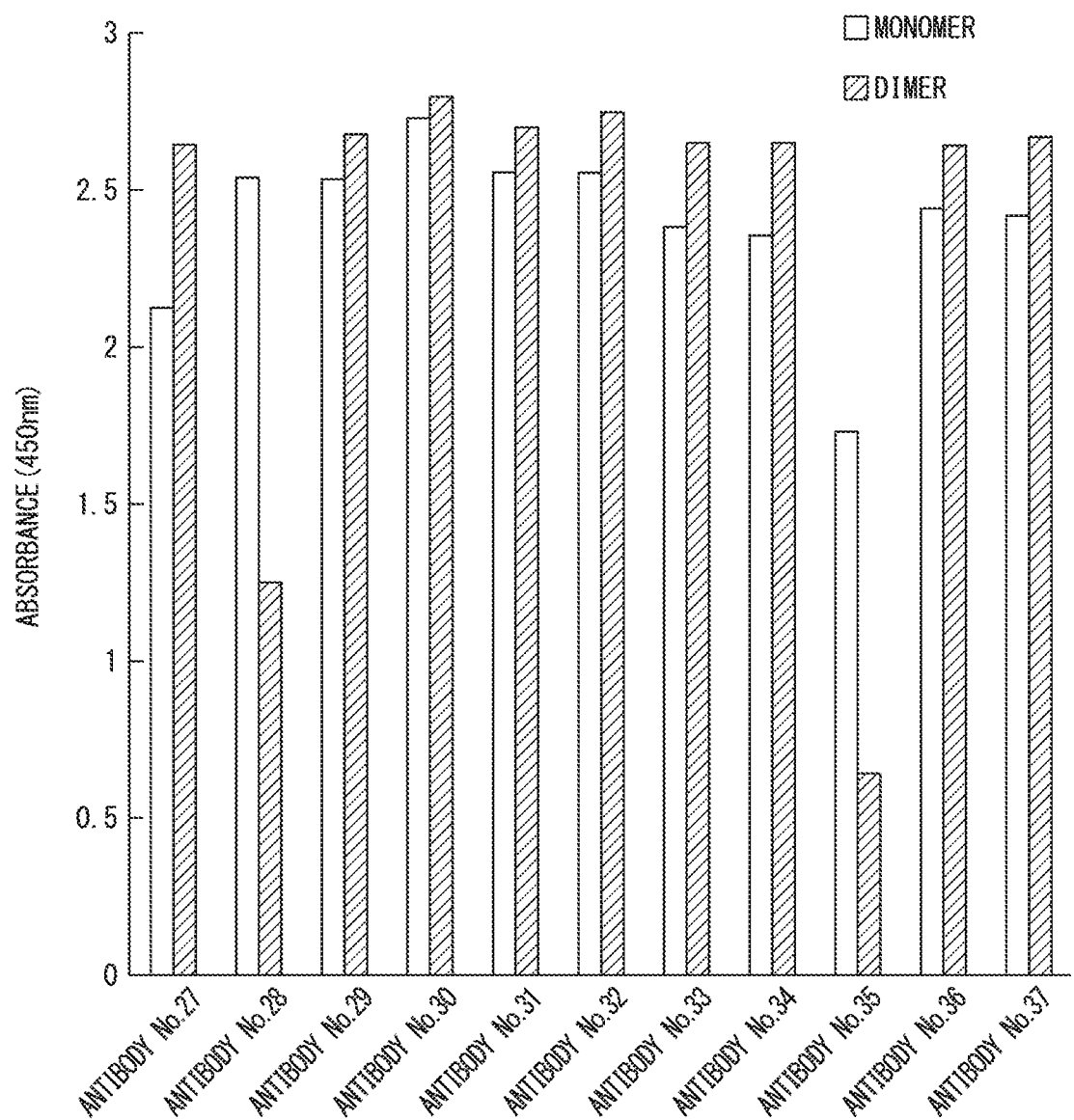
FIG. 1 is a figure representing reactivity of an anti-APOA4 monoclonal antibody of the present invention to a monomer and a dimer of rhAPOA4-His.

Hereinafter, embodiments of the present invention will be specifically described.

<APOA4>

The term "APOA4 gene" is a gene encoding an apolipoprotein A-IV, and is known to be expressed not only in humans but also in rodents such as mice and rats. Examples of the gene sequence encoding human APOA4 includes a base sequence registered under GenBank Accession No. NM_000482 or a base sequence represented by SEQ ID NO: 1. The amino acid sequence of human APOA4 includes an amino acid sequence registered under GenBank Accession No. NP_000473 or an amino acid sequence represented by SEQ ID NO: 2. Hereinafter, APOA4 refers to human APOA4 unless otherwise specified.

In an aspect of the present invention, APOA4 includes a peptide including the amino acid sequence represented by SEQ ID NO: 2, or a peptide represented by an amino acid sequence in which one or a plurality of amino acids have been substituted, added, or deleted in the amino acid sequence. In the present invention, the term "plurality" used for APOA4 is not limited as long as it retains functional properties equivalent to the peptide represented by the amino acid sequence on which it is based, but the plurality is 2 to 40, for example, 2 to 35, 2 to 30, 2 to 25, 2 to 20, 2 to 15, 2 to 10, or 2 to 5. In another aspect of the present invention, APOA4 includes a peptide represented by an amino acid sequence having at least 90% homology, for example, 91%, 92%, 93%, 94%, 95%, 96%, 97%, 98%, or 99% homology to the amino acid sequence represented by SEQ ID NO: 2.

In the present invention, the term "homology" of an amino acid sequence means homology in a case where a comparison between two sequences (Pairwise Alignment) is performed using the CLUSTALW algorithm under the following parameter settings.

K-tuple (word) size: 1
Window size: 5
Gap Penalty: 3
Number of Top Diagonals: 5
Scoring Method: PERCENT The APOA4 used in the present invention may be commercially available, may be extracted and generated from blood, or may be produced by genetic recombination technology. APOA4 by the genetic recombination technology can be produced by cloning a gene encoding APOA4, preparing a vector containing the gene, introducing the vector into a host cell for transformation to obtain a cell expressing APOA4, and culturing the cell. The cell used in the preparation, the kind of vector, the kind of cell, the culture conditions, and the like are within the technical range of those skilled in the art, and suitable conditions can be appropriately set.

In an embodiment of the present invention, in order to prepare a monoclonal antibody against human APOA4 including the amino acid sequence represented by SEQ ID NO: 2 and to use as a standard product in an immunological measurement method using the antibody, it is possible to use a recombinant human APOA4 (hereinafter, also referred to as rhAPOA4-His) in which a histidine tag is bound to a C-terminal of human APOA4. The cells used in preparation of rhAPOA4-His, the kind of vector, the kind of cell, culture conditions, and the like are within a technical range of those skilled in the art, and suitable conditions can be appropriately set.

<Monoclonal Antibody>

The term "antibody" in the present specification refers to a full-length immunoglobulin molecule that exists in nature or is produced by genetic recombination technology, and the term "antibody fragment" refers to an antigen-binding fragment of the immunoglobulin molecule. Such an antibody and antibody fragment can be prepared using a conventional technique. Examples of the antibody fragment include F(ab')2, F(ab)$_2$, Fab', Fab, Fv, scFv, variants thereof, a fusion protein or peptide including an antibody portion, and a modified structure other than an immunoglobulin molecule including an APOA4-binding site.

In the present specification, the term "specifically binds" means that the antibody binds to APOA4 without substantially binding to another polypeptide different from APOA4.

In the present invention, the term "monoclonal antibody" means an antibody obtained from a substantially homogeneous population, and an individual antibody contained in the population is identical except for a natural mutant that is likely to be present. The monoclonal antibody is an antibody exhibiting one binding specificity and affinity for a specific epitope of an antigen. The modifier "monoclonal" indicates properties of the antibody obtained from a substantially homogeneous antibody population, and is not to be construed as limiting as requiring production of the antibody by a specific method.

The term "heavy chain" of an antibody used in the present specification refers to a larger one of the two types of polypeptide chains present in all antibody molecules in conformation present in nature. The term "light chain" of an antibody refers to a smaller one of the two types of polypeptide chains present in all antibody molecules in conformation present in nature.

The term "anti-APOA4 antibody" used in the present specification refers to an antibody that binds to APOA4. The anti-APOA4 antibody of the present invention or the antibody fragment thereof is preferably an antibody or an antibody fragment thereof, each of which specifically binds to APOA4. In addition, the anti-APOA4 antibody of the present invention or the antibody fragment thereof is preferably an anti-APOA4 monoclonal antibody or an antibody fragment thereof.

In the present invention, the anti-APOA4 antibody may be of an optional class such as IgG, IgA, IgM or a subclass thereof, and is not limited to a specific class. Depending on an antibody amino acid sequence of a constant region of a heavy chain (referred to as H chain in some cases), immunoglobulins are classified into different classes. The five main classes of immunoglobulins include IgA, IgD, IgE, IgG, and IgM, some of which are, for example, further classified into subclasses (isotypes) such as IgG1, IgG2, IgG3, IgG4 (in the case of mice, IgG1, IgG2a, IgG2b, IgG2c, and IgG3), IgA1, and IgA2 (in the case of mice, IgA). The constant regions of the heavy chain corresponding to different classes of immunoglobulins are α chains, δ chains, ε chains, γ chains, and μ chains, respectively. In addition, in this kind of light chain (referred to as L chain in some cases) of the antibody, there exist λ chains and κ chains.

In the present invention, an antibody variable region means a variable region of the antibody light chain, a variable region of the antibody heavy chain, or both of the variable regions. In the present invention, the constant region of an antibody means the constant region of an antibody light chain, the constant region of an antibody heavy chain, or both of the constant regions. The variable regions of the heavy chain and the light chain consist of three complementarity determining regions (CDR) also known as hypervariable regions and four framework regions (FR) linked by the CDRs. The CDRs in each chain are held in the vicinity by the FRs, and contribute to the formation of an antigen-binding site of the antibody, together with the CDRs in other chains.

Technologies for determining CDRs include, but are not limited to, (1) an approach based on heterologous sequence variability (for example, Kabat et al. Sequencings of Proteins of Immunological interest, 5th ed., 1991, National Institutes of Health, Bethesda Md.); and (2) an approach based on crystallographic studies of the antigen-antibody complex (Al-lazikani et al., J. Molec. Biol. 273, 927-948, 1997), for example. These approaches and others may be used in combination.

The anti-APOA4 antibody or the antibody fragment thereof of the present invention can be prepared according to a known method. An anti-APOA4 monoclonal antibody or an antibody fragment thereof is obtained by isolating an antibody-producing cell from a non-human mammal immunized with APOA4 or an APOA4 fragment, fusing the antibody-producing cell with a myeloma cell or the like to produce a hybridoma, and purifying the antibody from which the hybridoma was produced. The APOA4 fragment is a partial peptide of APOA4, and a monoclonal antibody against the APOA4 fragment or an antibody fragment thereof binds to APOA4. Examples of the immunogen include APOA4 or APOA4 fragment such as from primates such as humans and monkeys, and rodents such as rats and mice, and preferably human APOA4 or APOA4 fragment.

In addition, the anti-APOA4 antibody or the antibody fragment thereof of the present invention can also be produced using a known genetic recombination technology.

Specifically, it is possible to produce the anti-APOA4 antibody or the antibody fragment thereof by cloning a gene encoding a monoclonal antibody produced by the hybridoma prepared above, a heavy chain variable region, a light chain variable region, a heavy chain CDR, a light chain CDR of the antibody, and the like, preparing a vector containing the gene, introducing the vector into a host cell for transformation to obtain a cell expressing the anti-APOA4 antibody or the antibody fragment thereof of the present invention, and culturing the cell. The cell used in the preparation, the kind of vector, the kind of cell, the culture conditions, and the like are within the technical range of those skilled in the art, and suitable conditions can be appropriately set.

Examples of the anti-APOA4 antibody or the antibody fragment thereof of the present invention include an anti-APOA4 monoclonal antibody or an antibody fragment thereof, each of which specifically binds to an amino acid sequence from an 89th to a 110th amino acid and an amino acid sequence from a 200th to a 224th amino acid of APOA4 including the amino acid sequence represented by SEQ ID NO: 2, an anti-APOA4 monoclonal antibody or an antibody fragment thereof, each of which specifically binds to an amino acid sequence from a 122nd to a 144th amino acid, an amino acid sequence from a 156th to a 177th amino acid, and an amino acid sequence from a 242nd to a 252nd amino acid of APOA4 including the amino acid sequence represented by SEQ ID NO: 2, and the like.

Examples of the anti-APOA4 monoclonal antibody or the antibody fragment thereof, each of which specifically binds to an amino acid sequence from an 89th to a 110th amino acid and an amino acid sequence from a 200th to a 224th amino acid of APOA4 including the amino acid sequence represented by SEQ ID NO: 2 include an anti-APOA4 monoclonal antibody No. 30 (hereinafter, abbreviated as antibody No. 30) or an antibody fragment thereof, each of which specifically binds to APOA4 including the amino acid sequence represented by SEQ ID NO: 2, including:

a heavy chain CDR1 including the amino acid sequence represented by SEQ ID NO: 3;
a heavy chain CDR2 including an amino acid sequence represented by SEQ ID NO: 4;
a heavy chain CDR3 including an amino acid sequence represented by SEQ ID NO: 5;
a light chain CDR1 including an amino acid sequence represented by SEQ ID NO: 15;
a light chain CDR2 including an amino acid sequence represented by SEQ ID NO: 16; and
a light chain CDR3 including an amino acid sequence represented by SEQ ID NO: 17.

Examples of the anti-APOA4 monoclonal antibody or the antibody fragment thereof, each of which specifically binds to an amino acid sequence from a 122nd to a 144th amino acid, an amino acid sequence from a 156th to a 177th amino acid, and an amino acid sequence from a 242nd to a 252nd amino acid of APOA4 including the amino acid sequence represented by SEQ ID NO: 2 include, for example, an anti-APOA4 monoclonal antibody No. 33 (hereinafter, abbreviated as antibody No. 33) or an antibody fragment thereof, each of which specifically binds to APOA4 including the amino acid sequence represented by SEQ ID NO: 2, including:

a heavy chain CDR1 including the amino acid sequence represented by SEQ ID NO: 6;
a heavy chain CDR2 including an amino acid sequence represented by SEQ ID NO: 7;
a heavy chain CDR3 including an amino acid sequence represented by SEQ ID NO: 8;
a light chain CDR1 including an amino acid sequence represented by SEQ ID NO: 18;
a light chain CDR2 including an amino acid sequence represented by SEQ ID NO: 19; and
a light chain CDR3 including an amino acid sequence represented by SEQ ID NO: 20.

Moreover, in addition to antibody No. 30, antibody No. 33, and the antibody fragments thereof, examples of the anti-APOA4 antibody of the present invention or the antibody fragment thereof includes an anti-APOA4 monoclonal antibody No. 36 (hereinafter, abbreviated as antibody No. 36) or an antibody fragment thereof, each of which specifically binds to APOA4 including the amino acid sequence represented by SEQ ID NO: 2, including:

a heavy chain CDR1 including the amino acid sequence represented by SEQ ID NO: 9;
a heavy chain CDR2 including an amino acid sequence represented by SEQ ID NO: 10;
a heavy chain CDR3 including an amino acid sequence represented by SEQ ID NO: 11;
a light chain CDR1 including an amino acid sequence represented by SEQ ID NO: 21;
a light chain CDR2 including an amino acid sequence represented by SEQ ID NO: 22; and
a light chain CDR3 including an amino acid sequence represented by SEQ ID NO: 23.

an anti-APOA4 monoclonal antibody No. 37 (hereinafter, abbreviated as antibody No. 37) or an antibody fragment thereof, each of which specifically binds to APOA4 including the amino acid sequence represented by SEQ ID NO: 2, including:

a heavy chain CDR1 including an amino acid sequence represented by SEQ ID NO: 12;
a heavy chain CDR2 including an amino acid sequence represented by SEQ ID NO: 13;
a heavy chain CDR3 including an amino acid sequence represented by SEQ ID NO: 14;
a light chain CDR1 including an amino acid sequence represented by SEQ ID NO: 24;
a light chain CDR2 including an amino acid sequence represented by SEQ ID NO: 25; and
a light chain CDR3 including an amino acid sequence represented by SEQ ID NO: 26.

An anti-APOA4 monoclonal antibody or an antibody fragment thereof, each of which specifically binds to APOA4 including the amino acid sequence represented by SEQ ID NO: 2, including these heavy chains CDR1 to CDR3 and light chains CDR1 to CDR3 can be produced by using a known genetic recombination technology. Specifically, it is possible to produce the anti-APOA4 monoclonal antibody or the antibody fragment thereof by incorporating the genes encoding the heavy chains CDR1 to CDR3 and the light chains CDR1 to CDR3 into a vector containing the genes encoding the FRs of the antibody and the constant regions of the antibody, respectively, introducing these into a host cell for transformation to obtain a cell expressing the antibody, and culturing the cell. The cell used in the preparation, the kind of vector, the kind of cell, the culture conditions, and the like are within the technical range of those skilled in the art, and suitable conditions can be appropriately set.

Antibody No. 30 includes a heavy chain variable region including the amino acid sequence represented by SEQ ID NO: 27 and a light chain variable region including the amino acid sequence represented by SEQ ID NO: 31.

Antibody No. 33 includes a heavy chain variable region including the amino acid sequence represented by SEQ ID NO: 28 and a light chain variable region including the amino acid sequence represented by SEQ ID NO: 32.

Antibody No. 36 includes a heavy chain variable region including the amino acid sequence represented by SEQ ID NO: 29 and a light chain variable region including the amino acid sequence represented by SEQ ID NO: 33.

Antibody No. 37 includes a heavy chain variable region including the amino acid sequence represented by SEQ ID NO: 30 and a light chain variable region including the amino acid sequence represented by SEQ ID NO: 34.

An anti-APOA4 monoclonal antibody or an antibody fragment thereof, each of which specifically binds to APOA4 including the amino acid sequence represented by SEQ ID NO: 2, including the heavy chain variable region and the light chain variable region, can be prepared by using a known genetic recombination technology. Specifically, the anti-APOA4 monoclonal antibody or the antibody fragment thereof can be produced by incorporating genes encoding a heavy chain variable region and a light chain variable region into a vector containing a gene encoding constant regions of the antibody, introducing the genes into a host cell for transformation to obtain a cell expressing the antibody, and culturing the cell. The cell used in the preparation, the kind of vector, the kind of cell, the culture conditions, and the like are within the technical range of those skilled in the art, and suitable conditions can be appropriately set.

All of antibody No. 30, antibody No. 33, antibody No. 36, antibody No. 37, and the antibody fragments thereof specifically bind to monomers and dimers of APOA4.

<Measurement Method>

In an embodiment of the present invention, a measurement method for measuring APOA4 is a measurement method for immunologically measuring APOA4 in a specimen, in which APOA4 in the specimen is bound to a capture antibody that specifically binds to the APOA4, a labeled detection antibody in which a label is bound to a detection antibody that specifically binds to the APOA4 is added to form an immune complex consisting of the APOA4, the capture antibody, and the labeled detection antibody, and an amount of label in the formed immune complex is measured. Here, the term "capture antibody" and the term "detection antibody" are an anti-APOA4 antibody or an antibody fragment thereof that specifically binds to APOA4, and preferably an anti-APOA4 monoclonal antibody or an antibody fragment thereof.

In a method for measuring APOA4 in a specimen of the present invention, examples of the specimen include a body fluid and the like, and examples of the body fluid include, non-restrictively, blood such as serum, plasma or whole blood, a lymphatic fluid, a tissue fluid, a cerebrospinal fluid, a body cavity fluid, a digestive juice, a runny nose, tears, sweats, urine, and the like, but are not limited thereto. From a viewpoint of convenience of obtainment and processing, it is preferable to use serum or plasma as the specimen. In addition, the body fluid may be a body fluid itself collected from a subject, or a body fluid obtained by subjecting the collected body fluid to a processing such as dilution and concentration that is usually performed. In addition, the specimen used in the present invention may be collected or prepared at a time of carrying out the present invention, or may be collected or prepared in advance and stored.

The immunological measurement method can be classified into an enzyme immunoassay (EIA or ELISA), a radioimmunoassay (RIA), a fluorescence immunoassay (FIA), a fluorescence polarization immunoassay (FPIA), a chemiluminescence immunoassay (CLIA), and an electrochemiluminescence immunoassay, and the like, depending on the label of the labeled detection antibody, and all of these can be used in the measurement method of the present invention. However, ELISA is preferable since it is possible to conveniently and quickly measure the detection target.

In the immunological measurement method of the present invention, the capture antibody is preferably immobilized on a solid support. An appropriately processed biological sample is added to the capture antibody immobilized on a solid support and reacted, and a labeled detection antibody is further added in which a label is bound to the detection antibody specifically binding to APOA4, different from the capture antibody to form an immune complex consisting of the APOA4, the capture antibody, and the labeled detection antibody.

The solid support is not particularly limited as long as the solid support can reliably hold an antibody or an antibody fragment. Examples of the preferable material of the solid support include polymer materials such as polystyrene, polycarbonate, polyvinyl toluene, polypropylene, polyethylene, polyvinyl chloride, nylon, polymethacrylate, gelatin, agarose, cellulose, nitrocellulose, cellulose acetate, and polyethylene terephthalate, glass, ceramics, magnetic particles, metal, and the like. Examples of the preferable shape of the solid support include a tube, a bead, a plate, fine particles such as latex, sticks, and the like.

After washing the immune complex, the label in the immune complex is measured to measure the APOA4 in the specimen. For example, in a case of ELISA, the APOA4 in the specimen can be measured by reacting an enzyme which is a label with a substrate of the enzyme and measuring the absorbance of a colored product. In addition, the APOA4 in the specimen can be measured by reacting the capture antibody immobilized on the solid support with APOA4 in the specimen, adding an unlabeled anti-APOA4 antibody or an antibody fragment thereof (primary antibody), further adding the antibody against the primary antibody labeled with an enzyme or an antibody fragment thereof (secondary antibody), and measuring a label of the secondary antibody. In addition, the APOA4 in the specimen can be measured by labeling the secondary antibody with biotin, binding avidin or streptavidin labeled with an enzyme or the like to biotin, thereby labeling the secondary antibody with the enzyme and the like, and measuring the label of the secondary antibody.

As the label, it is possible to use an enzyme such as peroxidase and alkaline phosphatase in ELISA, a radioactive substance such as $^{125}I$, $^{131}I$, $^{35}S$ and $^{3}H$ in RIA, and a fluorescent substance such as fluorescein isothiocyanate, rhodamine, dansyl chloride, phycoerythrin, tetramethyl rhodamine isothiocyanate, and a near-infrared fluorescent material in FPIA, an enzyme such as luciferase and β-galactosidase and a luminescent substrate that is converted into a luminescent substance by each enzyme, and a luminescent substance such as luciferin and aequorin in CLIA method. In addition, nanoparticles such as colloidal gold and quantum dots can be used as labels.

In ELISA, as the substrate of the enzyme which is a label, in a case where the enzyme is peroxidase, 3,3'-diaminobenzidine (DAB), 3,3',5,5'-tetramethylbenzidine (TMB), O-phenylenediamine (OPD), and the like can be used, and in a case where the enzyme is alkaline phosphatase, p-nitrophenyl phosphate (pNPP) and the like can be used.

Examples of the capture antibody that specifically binds to the APOA4 include an anti-APOA4 monoclonal antibody or an antibody fragment thereof, each of which specifically binds to an amino acid sequence from an 89th to a 110th amino acid and an amino acid sequence from a 200th to a 224th amino acid of APOA4 including the amino acid sequence represented by SEQ ID NO: 2. As the capture antibody, an anti-APOA4 antibody or an antibody fragment thereof, each of which specifically binds to a monomer and a dimer of APOA4 is preferable, for example, antibody No. 30, antibody No. 33, antibody No. 36, antibody No. 37, and antibody fragments thereof and the like, but antibody No. 30 or the antibody fragment thereof is preferable.

In addition, examples of the detection antibody that specifically binds to APOA4, different from the capture antibody, include an anti-APOA4 antibody or an antibody fragment thereof that binds to an epitope different from that of the capture antibody, and for example, an anti-APOA4 monoclonal antibody or an antibody fragment thereof, each of which specifically binds to an amino acid sequence from a 122nd to a 144th amino acid, an amino acid sequence from a 156th to a 177th amino acid, and an amino acid sequence from a 242nd to a 252nd amino acid of APOA4 including the amino acid sequence represented by SEQ ID NO: 2 and the like are exemplified. As the detection antibody, an anti-APOA4 antibody or an antibody fragment thereof, each of which specifically binds to a monomer of APOA4 is preferable. For example, antibody No. 30, antibody No. 33, antibody No. 36, antibody No. 37, antibody fragments thereof, and the like are exemplified, but antibody No. 33, antibody No. 36, antibody No. 37, or antibody fragment thereof is preferable, and antibody No. 33 or the antibody fragment thereof is more preferable.

The combination of the capture antibody and the detection antibody is not particularly limited as long as the capture antibody and the detection antibody are different from each other. For example, a combination in which the capture antibody is set as antibody No. 30 or the antibody fragment thereof and the detection antibody is set as antibody No. 33 or antibody fragment thereof, a combination in which the capture antibody is set as antibody No. 30 or the antibody fragment thereof and the detection antibody is antibody No. 36 or the antibody fragment thereof, a combination in which the capture antibody is set as antibody No. 30 or the antibody fragment thereof and the detection antibody is set as antibody No. 37 or the antibody fragment thereof, and a combination in which the capture antibody is set as antibody No. 30 or the antibody fragment thereof and the detection antibody is set as antibody No. 33 or the antibody fragment thereof are preferable.

<Kit>

The kit of the present invention is a kit used for the measurement method of APOA4 of the present invention, and includes a capture antibody that specifically binds to APOA4 including the amino acid sequence represented by SEQ ID NO: 2 and a labeled detection antibody in which a label is bound to a detection antibody that specifically binds to the APOA4.

The capture antibody and the detection antibody used in the kit of the present invention are different from each other. For example, the capture antibody and the detection antibody each bind to different epitopes on APOA4.

Examples of the capture antibody and the detection antibody used in the kit of the present invention include the capture antibody and the detection antibody exemplified in the section of <Measurement method>. In addition, examples of the combination of the capture antibody and the detection antibody used in the kit of the present invention include the combinations of the capture antibody and the detection antibody exemplified in the section of <Measurement method>.

The kit of the present invention may further include a reagent and an apparatus required for measuring APOA4 in a specimen by a measurement method for immunologically measuring APOA4 in the specimen of the present invention.

In an embodiment, the kit of the present invention includes, in addition to the capture antibody and the labeled detection antibody, a solid support such as a microtiter plate and a reagent for measuring a label. In a case where the label is an enzyme, examples of the reagent for measuring the label include a substrate of alkaline phosphatase such as p-nitrophenyl phosphate (pNPP), a substrate of peroxidase such as 3,3'-diaminobenzidine tetrahydrochloride (DAB), 3,3',5,5'-tetramethylbenzidine (TMB), o-phenylenediamine dihydrochloride (OPD), and the like.

In the case of such a kit, first, the capture antibody is immobilized on a solid support such as a microtiter plate, an appropriately processed and diluted specimen is added hereto and incubated, and then a specimen not bound to the capture antibody is removed by washing. Subsequently, a labeled detection antibody is added and incubated, and the label on the solid support is measured. For example, in a case where the label is an enzyme, it is possible to measure APOA4 in the specimen by adding a substrate of the enzyme and performing coloring, and measuring the coloring by using a microtiter plate reader and the like.

In another embodiment, the kit of the present invention may include a secondary antibody that is an antibody or an antibody fragment that binds to an anti-APOA4 antibody or an antibody fragment thereof. Examples of such a kit include a kit including a solid support such as a microtiter plate, a capture antibody, an anti-APOA4 antibody as a primary antibody, a labeled secondary antibody labeled with an enzyme such as alkaline phosphatase and peroxidase against an anti-APOA4 antibody or an antibody fragment thereof, a substrate of alkaline phosphatase such as pNPP, or a substrate of peroxidase such as DAB, TMB, and OPD.

In a case of such a kit, first, the capture antibody is immobilized on a solid support such as a microtiter plate, an appropriately processed and diluted specimen is added hereto and incubated, and the specimen not bound to the capture antibody is removed by washing. Subsequently, the primary antibody is added and incubated, washing is performed, and further an enzyme-labeled secondary antibody that recognizes the primary antibody is added and incubated. Thereafter, it is possible to measure APOA4 in a specimen by adding a substrate of the enzyme that is a label and coloring, and measuring the coloring by using a microtiter plate reader and the like. By using such a secondary antibody, the reaction is amplified and the detection sensitivity can be increased.

The kit of the present invention may further include a necessary buffer, an enzyme reaction stop solution, a microplate reader, a product description, and the like.

The label is not particularly limited, and examples thereof include an enzyme such as peroxidase and alkaline phosphatase, a radioactive substance such as $^{125}I$, $^{131}I$, $^{35}S$, and $^{3}H$, a fluorescent substance such as fluorescein isothiocyanate, rhodamine, dansyl chloride, phycoerythrin, tetramethylrhodamine isothiocyanate, and a near-infrared fluorescent material, a luminescent substance such as luciferase, luciferin, and aequorin, and nanoparticles such as colloidal gold and quantum dots. In addition, the kit can include a labeled avidin or streptavidin by using a biotinylated anti-APOA4 antibody or an antibody fragment thereof as a detection antibody.

The terms used in the present specification are used for describing specific embodiments, and are not intended to limit the invention.

In addition, the term "including" as used in the present specification is intended to describe the stated matter (member, step, element, number, and the like), except for a case of requiring a clearly different understanding in context, and does not exclude that other matters (member, step, element, number, and the like) are present.

Unless otherwise defined, all terms (including technical terms and scientific terms) used herein have the same meaning as widely understood by those skilled in the art to which this invention belongs. As long as a different definition is not clarified, the terms used herein should be construed as having a meaning consistent with the meaning in the present specification and the related technical field, and should not be interpreted in an idealized, or excessively formalized meaning.

EXAMPLES

Hereinafter, the present invention will be described more specifically with reference to examples. However, the present invention may be embodied in various forms and should not be construed as limited to the embodiments set forth herein.

Example 1: Preparation of Histidine Tag-Binding Recombinant Human APOA4

In order to prepare a monoclonal antibody against human APOA4 including the amino acid sequence represented by SEQ ID NO: 2, a recombinant protein in which a histidine tag was bound to the C-terminal of human APOA4 was prepared by the following steps.

A gene encoding human APOA4 was amplified from cDNA of human liver by PCR. The gene was inserted into the HindIII/NotI site of the pcDNA 3.4 vector (manufactured by ThermoFisher Scientific) into which the gene encoding the histidine tag was inserted. The prepared vector was transformed into Expi293F cells according to a standard method of Expi293 Expression System (manufactured by ThermoFisher Scientific), and a recombinant protein (referred to as rhAPOA4-His) in which a histidine tag was bound to the C-terminal of human APOA4 was secreted in a culture supernatant. The rhAPOA4-His secreted in the culture supernatant was purified from the culture supernatant with TALON Superflow Metal Affinity Resin (manufactured by CLONTECH) and then dialyzed against D-PBS (manufactured by Wako Pure Chemical Industries).

Example 2: Preparation of rhAPOA4-his Monomer and Dimer

The rhAPOA4-His purified in Example 1 was subjected to size exclusion chromatography (SEC) to perform size fractionation. The SEC column was performed at 4° C. using Superdex 200/10/300 GL (manufactured by GE Healthcare) connected to an AKTA explorer10s chromatography system. D-PBS (−) (manufactured by Wako Pure Chemical Industries, Ltd.) was used as a solvent and a flow rate was 0.5 ml/min. An elution profile of the protein was detected at an absorbance of 280 nm, and the elution fraction was collected in 0.3 mL portions into a 96-well plate. The elution fraction was recovered using the peak of Retention 11.8 ml as a dimer and the peak of Retention 14.2 ml as a monomer. The protein mass of the dimer and the monomer fraction was calculated from a calibration curve using bovine serum albumin (BSA) of known concentration as a standard substance using Micro BCA Protein Assay Kit (manufactured by ThermoFisher Scientific).

Example 3: Preparation of Mouse Anti-Human APOA4 Monoclonal Antibody-Producing Hybridoma (1) Preparation of Hybridoma 10 μg of rhAPOA4-His was mixed with an equal amount of TiterMax Gold Adjuvant (manufactured by TiterMax USA) or Magic Mouse Adjuvant (manufactured by Creative Diagnostics), and subcutaneously injected into a footpad of C57BL/6J and Balb/cA mouse. Thereafter, on the 3rd, 7th, 10th, 17th, 25th, and 31st days, rhAPOA4-His was similarly administered. At this time, TiterMax Gold Adjuvant (TiterMax USA) and Magic Mouse Adjuvant (manufactured by Creative Diagnostics) were used on the 3rd, 10th, 17th, and 31st days. On the 34th day, the mouse was sacrificed and peripheral lymph nodes were recovered to prepare lymph node cells. The prepared lymph node cells and P3U1 myeloma cells were fused at a ratio of 5:1 in the presence of GenomeONE-CF (manufactured by Ishihara Sangyo Co., Ltd.). The hybridoma was cultured in a 96-well plastic plate. After incubation at 5% $CO_2$ and 37° C. for 7 days, the culture supernatant was recovered.

(2) Screening of Anti-Human APOA4 Monoclonal Antibody-Producing Hybridoma

Using the culture supernatant of the hybridoma obtained in (1), the reactivity to rhAPOA4-His was evaluated by ELISA as follows.

50 μL/well of a 50 mM Tris buffer (pH 7.5) containing 2 μg/mL of an anti-6× His rabbit polyclonal antibody (anti-6×His antibody, manufactured by Bethyl Laboratories) was added to a 96-well plate (manufactured by Nunc), and incubation was performed at 4° C. overnight. After removing the anti-6×His antibody solution, blocking was performed by adding 100 μL/well of 50 mM Tris-buffered saline solution (pH 7.5) containing 0.01% Tween 20 and 5% skim milk, and the plate was left at room temperature for 1 hour. After washing the well three times with Tris-buffered saline solution (pH 7.5) (washing solution) containing 0.01% Tween 20, rhAPOA4-His prepared in Example 1 or refolded rhAPOA4-His monomer prepared by the method described below was added at a concentration of 450 ng/mL (10 nM) by 50 μL/well, and incubation was performed at room temperature for 1 hour. The refolded rhAPOA4-His monomer was prepared by diluting rhAPOA4-His prepared in Example 1 two-fold with a 50 mM Tris-buffered saline solution (pH 7.5) containing 8 M urea (manufactured by Wako Pure Chemical Industries, Ltd.), leaving at room temperature for 30 minutes, and diluting 50-fold with a 50 mM Tris-buffered saline solution (pH 7.5) (reaction solution) containing 4% Block Ace (manufactured by DS Pharma Biomedical Corporation) and 0.01% Tween 20. After washing the well three times with the washing solution, the culture supernatant of the hybridoma was added to the well and incubation was performed at room temperature for 1 hour. After removing the added culture supernatant, the well was washed three times with the washing solution. A horseradish peroxidase-labeled anti-mouse IgG antibody (manufactured by Jackson ImmunoResearch Laboratories) appropriately diluted with the reaction solution was added at 50 μL/well, incubation was performed at room temperature for 1 hour, and then the well was washed 5 times with the washing solution. 50 μL/well of a TMB (3,3',5,5'-tetramethylbenzidine) solution was added and incubation was performed at room temperature for 30 minutes. The reaction was stopped by adding 50 μL/well of 1N $H_2SO_4$ in the equivalent volume to that of the TMB solution, and the absorbance of 450 nm was measured using a microplate reader (manufactured by PerkinElmer Corporation).

(3) Cloning of Hybridoma Expressing Mouse Anti-Human APOA4 Antibody

In the above (2), a hybridoma was cloned by a limiting dilution method from a well containing a culture supernatant of a hybridoma exhibiting reactivity to rhAPOA4-His to obtain a hybridoma clone expressing a mouse anti-human APOA4 antibody having reaction activity to a refolded rhAPOA4-His monomer.

(4) Purification of Anti-Human APOA4 Monoclonal Antibody

The obtained hybridoma clone was cultured, and anti-human APOA4 monoclonal antibodies No. 27 to No. 37 was obtained by purification from the culture supernatant using Protein A (manufactured by GE Healthcare).

Example 4: Reactivity of Anti-Human APOA4 Monoclonal Antibody to rhAPOA4-his Monomer and Dimer 50 μL/well of a 50 mM Tris buffer (pH 7.5) containing 2 μg/mL of an anti-6×His rabbit polyclonal antibody (anti-6× His antibody, manufactured by Bethyl Laboratories) was added to a 96-well plate (manufactured by Nunc), and incubation was performed at 4° C. overnight. After removing the anti-6×His antibody solution, blocking was performed by adding 100 μL/well of 50 mM Tris-buffered saline solution (pH 7.5) containing 0.01% Tween 20 and 5% skim milk, and the plate was left at room temperature for 1 hour. After washing the well three times with a Tris-buffered saline solution (pH 7.5) (washing solution) containing 0.01% Tween 20, the rhAPOA4-His monomer or dimer prepared in Example 2 was diluted so as to be 450 ng/mL with a 50 mM Tris-buffered saline solution (pH 7.5) (reaction solution) containing 1% Block Ace (manufactured by DS Pharma Biomedical) and 0.01% Tween 20, and added thereto at 50 μL/well. After incubating at room temperature for 1 hour, the well was washed three times with the washing solution, and then the anti-human APOA4 monoclonal antibody obtained in Example 3 was diluted with the reaction solution so as to be 1 μg/mL and added thereto at 50 μL/well. After the incubation at room temperature for 1 hour, the well was washed three times with the washing solution. Subsequently, 50 μL/well of a horseradish peroxidase-labeled anti-mouse IgG antibody (manufactured by Jackson ImmunoResearch Laboratories) appropriately diluted with the reaction solution was added, incubation was performed at room temperature for 1 hour, and the well was washed 5 times with the washing solution. 50 μL/well of a TMB (3,3',5,5'-tetramethylbenzidine) solution was added and incubation was performed at room temperature for 15 minutes. The reaction was stopped by adding 50 μL/well of 1N $H_2SO_4$ in the equivalent volume to that of the TMB solution, and the absorbance of 450 nm was measured using a microplate reader (manufactured by ThermoFisher Scientific).

The reactivity of anti-human APOA4 monoclonal antibodies No. 27 to No. 37 to the APOA4 monomer and dimer are shown in FIG. 1.

Example 5: Analysis of APOA4 Monomer and Dimer in Human Serum

Two serum samples (N65S and N67S) were used as human specimens. 150 μL of serum stored at 4° C. or −80° C. for 2 weeks after separation was subjected to size exclusion chromatography (SEC) to perform size fractionation. APOA4 in the eluted fraction was detected by Western blotting. The SEC column was performed at 4° C. using Superdex 200 10/300 GL (manufactured by GE Healthcare) connected to an AKTA pure25 chromatography system. D-PBS (−) (manufactured by Wako Pure Chemical Industries, Ltd.) was used as a solvent and a flow rate was 0.5 ml/min. The elution profile of APOA4 was detected by absorbance of 280 nm, and the eluted fraction was collected in 0.3 mL portions into a 96-well plate. In order to confirm an elution position of APOA4 and measure a mass of APOA4 protein in each fraction, fractions 1 to 16 (for 32 wells) collected from a point (C1) at which protein elution was started by two wells were applied to SDS-PAGE. 15 μL of all the fractions diluted 1.5-fold with a 3×SDS sample buffer, and, as a standard substance for measuring APOA4 protein, a dilution series of rhAPOA4-His of known concentration was applied to each lane of Criterion TGX 4-20% gel. The detection of APOA4 by Western blotting was performed according to the following steps.

The gel after electrophoresis was transferred onto a nitrocellulose membrane using an iBLOT2 dry blotting system (manufactured by ThermoFisher Scientific), and shaking was performed in a 50 mM Tris-buffered saline solution containing 5% skim milk and 0.05% Tween 20 (hereinafter, referred to as a blocking solution) at room temperature for 1 hour or more, and blocking was performed. Using a rabbit polyclonal anti-APOA4 antibody (#70R-5429, manufactured by Fitzgerald Corporation) diluted with the blocking solution as a primary antibody, shaking was performed at 4° C. overnight. After washing three times with a 50 mM Tris-buffered saline solution (washing solution) containing 0.05% Tween 20, shaking was performed at room temperature for 1 hour using a horseradish peroxidase-labeled donkey anti-rabbit IgG (manufactured by Jackson ImmunoResearch Laboratories) diluted with the blocking solution as a secondary antibody. A chemiluminescent substrate (manufactured by ThermoFisher Scientific) was reacted with a membrane after washing four times with the washing solution, and a luminescence signal was detected with a CCD imager (manufactured by BIO-RAD Corporation).

Figure 2:
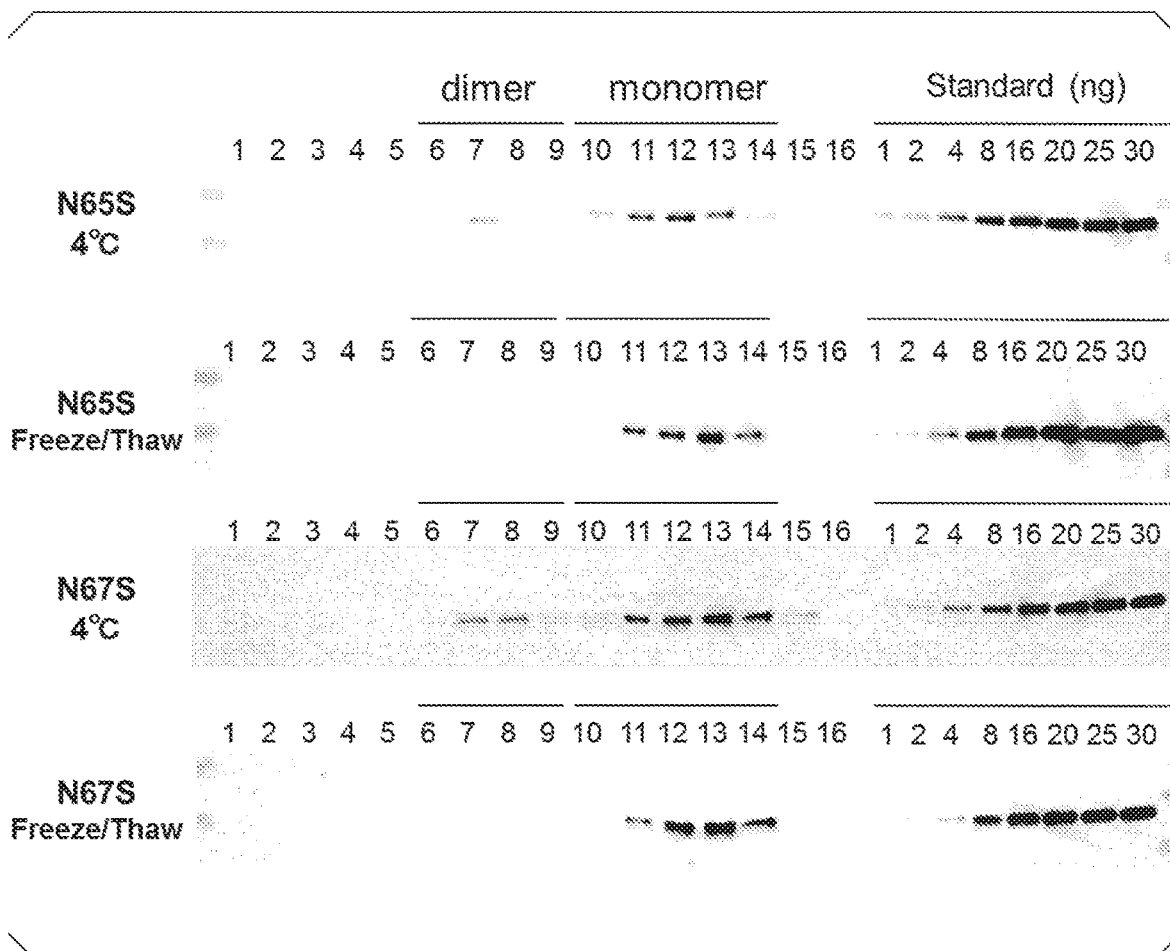
FIG. 2 is a figure representing an analysis result of monomers and dimers of APOA4 in human serum by Western blotting.

The detected protein mass of an APOA4 band was quantified using ImageLab Software (manufactured by BIO-RAD Corporation) from the band intensity of the dilution series of the standard substance electrophoresed on the same gel, and a ratio of a dimer eluted in fractions 6 to 9 and a monomer eluted in fractions 10 to 14 was calculated. The result of SEC is shown in FIG. 2. The dimer in the serum stored at 4° C. was contained 17.9% in N65S and 17.0% in N67S, respectively, while the dimer in the freeze-thawed serum was contained 0% and 0.08%, respectively.

Example 6: Preparation of Peroxidase-Labeled Monoclonal Antibody

Anti-human APOA4 monoclonal antibodies No. 33, No. 36 and No. 37 were labeled with Peroxidase (HRP: Horseradish Peroxidase) using Peroxidase Labeling Kit-NH2 (manufactured by Dojindo Laboratories) (hereinafter, referred to as "HRP-labeled antibody No. 33", "HRP-labeled antibody No. 36", and "HRP-labeled antibody No. 37", respectively).

Example 7: Measurement of Human Serum APOA4 by ELISA

Anti-human APOA monoclonal antibody No. 30 was adjusted to a concentration of 2 μg/mL with a 50 mM Tris buffer solution (pH 7.5). Antibody No. 30 solution was added to a Maxisorp cup (NUNC, manufactured by C8 Maxisorp) at 100 µL/well, the Maxisorp cup was put in a wet box and allowed to stand at 4° C. overnight, and antibody No. 30 was coated on the well. After removing antibody No. 30 solution by suction, a 50 mM Tris-buffered saline solution (pH 7.5) (blocking solution) containing 5% skim milk, 0.1% sodium azide, and 0.01% Tween 20 was added at 200 µL/well, and then the cup was left at room temperature for 2 hours or at 4° C. for 1 day or more (hereinafter, the prepared Maxisorp cup is referred to as "antibody No. 30 cup"). After removing the blocking solution by suction, antibody No. 30 cup was washed 3 times with a 50 mM Tris-buffered saline solution (pH 7.5) (washing solution) containing 0.01% Tween 20, a human serum sample (N64 to N68) frozen and stored at −80° C. for one day or two weeks was thawed, appropriately diluted with a 50 mM Tris-buffered saline solution (pH 7.5) (reaction solution) containing 4% Block Ace (DS Pharma Biomedical), 0.2% ProClin 150 (SIGMA-ALDRICH), and 0.01% Tween20 and added at 100 µL/well, and reaction was performed at room temperature for 2 hours. After washing three times with the washing solution, HRP-labeled antibody No. 33 diluted 5000-fold with the reaction solution was added at 100 µL/well, and reaction was performed at room temperature for 1 hour. After washing three times with the washing solution, 100 µL/well of 3,3',5,5'-tetramethylbenzidine (TMB) Liquid Substrate System for ELISA (manufactured by SIGMA-ALDRICH) was added and reaction was performed at room temperature for 30 minutes. After stopping the reaction by injecting 100 µL/well of 0.5 M $H_2SO_4$, the absorbance was measured at a wavelength of 450 nm, and an APOA concentration was calculated using the rhAPOA4-His of a known concentration as a standard substance. The result is shown in FIG. 3.

Figure 3:
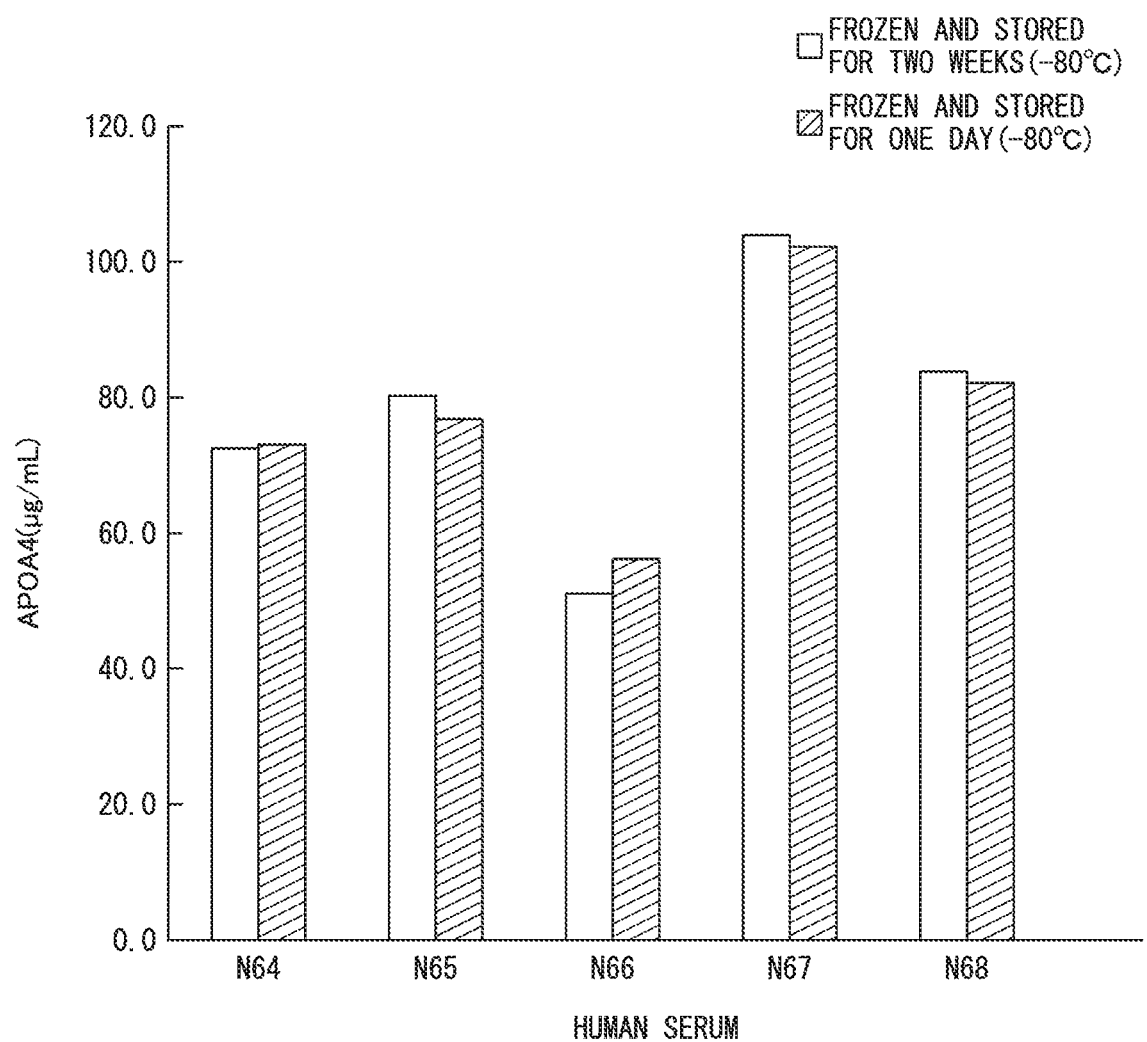
FIG. 3 is a figure representing a result of measuring APOA4 in human serum by ELISA using the anti-APOA4 monoclonal antibody of the present invention.

As shown in FIG. 3, it was confirmed that APOA4 in the frozen and stored serum can be measured by ELISA using antibody No. 30 as a capture antibody and HRP-labeled antibody No. 33 as a labeled detection antibody.

Example 8: Specimen Dilution Test

Except that samples for specimen dilution test obtained by diluting serum samples (N54 to N61) of 8 healthy humans 32,000-fold, 64,000-fold, 128,000-fold, and 256,000-fold with the reaction solution were used instead of serum samples, ELISA using antibody No. 30 as a capture antibody and HRP-labeled antibody No. 33 as a labeled detection antibody and ELISA using antibody No. 30 as a capture antibody and HRP-labeled antibody No. 37 as a labeled detection antibody were performed in the same manner as in Example 6 to measure APOA4 in a sample for specimen dilution test. The results are shown in FIGS. 4A and 4C.

In addition, except that samples for specimen dilution test obtained by diluting serum samples (N54 to N61) of 8 healthy humans 16,000-fold, 32,000-fold, 64,000-fold, and 128,000-fold with the reaction solution were used instead of serum samples, ELISA using antibody No. 30 as a capture antibody and HRP-labeled antibody No. 36 as a labeled detection antibody was performed in the same manner as in Example 6 to measure APOA4 in a sample for specimen dilution test. The result is shown in FIG. 4.

The ideal curve is a graph in which numerical values of the double series are entered. If the graph of the actual measurement value of the sample for specimen dilution test is parallel to the graph of the ideal curve, it indicates that the result is an accurate dilution test result.

Figure 4:
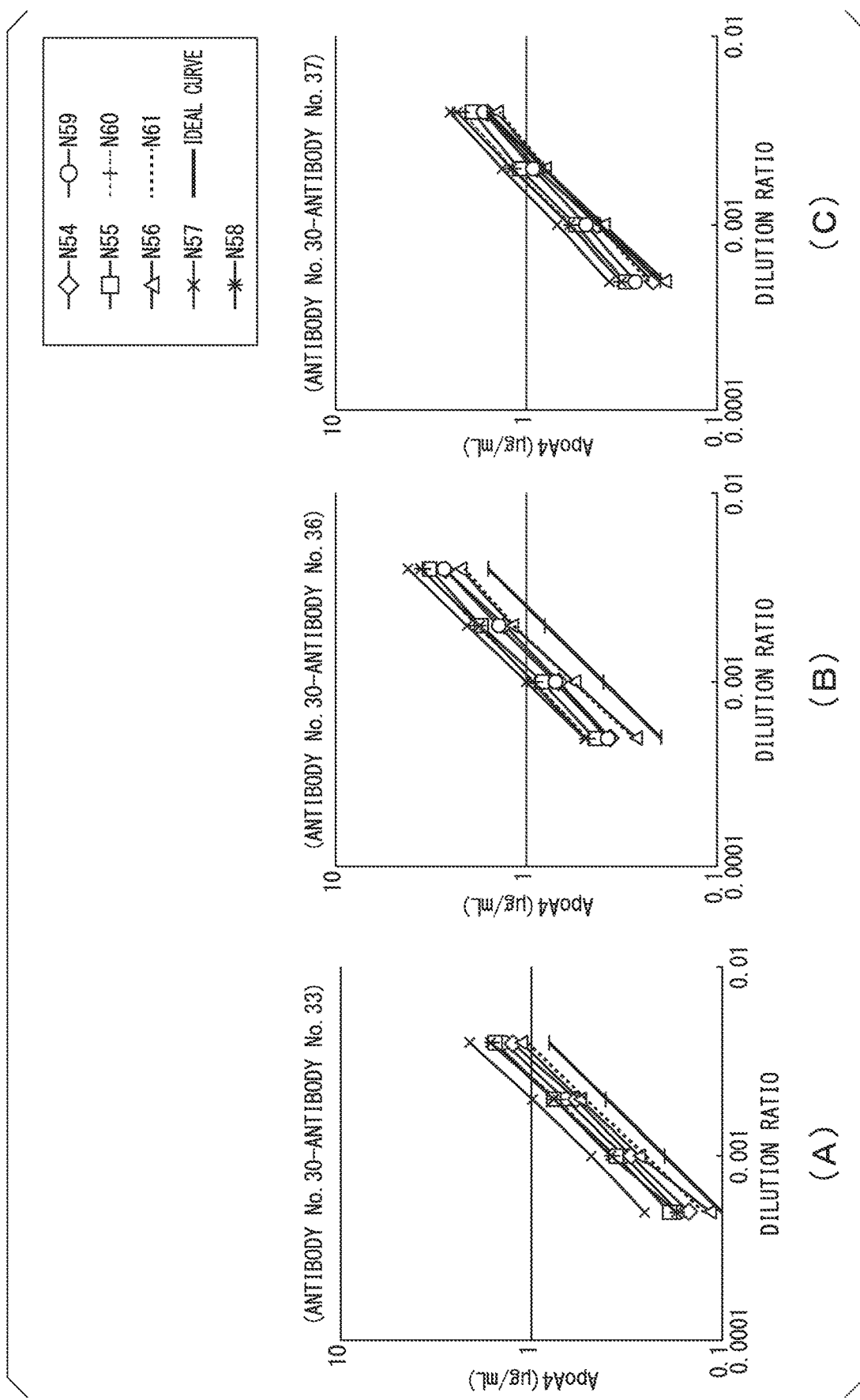
FIG. 4 is a figure representing a result of measuring APOA4 in a sample for specimen dilution by ELISA using the anti-APOA4 monoclonal antibody of the present invention.

As shown in FIG. 4, compared to the ideal curve indicating numerical values of the double series in a graph, in any of ELISA, the dilution line was a straight line parallel to the ideal curve. Therefore, it was confirmed that APOA4 in a specimen was accurately measured according to the dilution ratio of the specimen within the tested range.

Example 9: Addition Recovery Test

Except that a mixture specimen in which 1 ng/mL or 2 ng/mL of rhAPOA-His as a standard substance and a diluted specimen obtained by diluting serum samples (N54 to N61) of 8 healthy humans 32,000-fold or 64000-fold with the reaction solution are mixed in an equivalent amount was used instead of a sample for specimen dilution test, processing was performed in the same manner as in Example 7 to measure APOA4 in the mixture specimen. In addition, APOA4 in the standard substance and in the diluted specimen were measured in the same manner, and the addition recovery rate (%) calculated by the following equation was calculated in each ELISA. The closer the addition recovery rate is to 100%, the more accurate the measurement can be made.

Addition recovery rate (%)=(actual measurement value of mixed specimen−measured value of diluted specimen)/measured value of standard substance×100

Table 1 shows ELISA using antibody No. 30 as a capture antibody and HRP-labeled antibody No. 33 antibody as a labeled detection antibody, Table 2 shows ELISA using antibody No. 30 as a capture antibody and HRP-labeled antibody No. 36 as a labeled detection antibody, and Table 3 shows ELISA using antibody No. 30 as a capture antibody and HRP-labeled antibody No. 37 as a labeled detection antibody.

TABLE 1

| Capture antibody: antibody No. 30, detection antibody: antibody No. 33 | | | | | |
|---|---|---|---|---|---|
| Serum specimen | Measured value of diluted specimen | Measured value of standard substance | Measured value of mixed specimen (theoretical value) | Measured value of mixed specimen (actual measurement value) | Addition recovery rate (%) |
| N54 | 0.300 | 0.495 | 0.795 | 0.740 | 89.0 |
| N55 | 0.358 | 0.495 | 0.853 | 0.809 | 91.2 |
| N56 | 0.269 | 0.495 | 0.764 | 0.728 | 92.8 |
| N57 | 0.487 | 0.495 | 0.982 | 0.895 | 82.5 |
| N58 | 0.381 | 0.495 | 0.876 | 0.817 | 88.2 |

TABLE 1-continued

Capture antibody: antibody No. 30, detection antibody: antibody No. 33

| Serum specimen | Measured value of diluted specimen | Measured value of standard substance | Measured value of mixed specimen (theoretical value) | Measured value of mixed specimen (actual measurement value) | Addition recovery rate (%) |
|---|---|---|---|---|---|
| N59 | 0.328 | 0.495 | 0.823 | 0.809 | 97.3 |
| N60 | 0.384 | 0.495 | 0.879 | 0.830 | 90.2 |
| N61 | 0.253 | 0.495 | 0.748 | 0.715 | 93.4 |

TABLE 2

Capture antibody: antibody No. 30, detection antibody: antibody No. 36

| Serum specimen | Measured value of diluted specimen | Measured value of standard substance | Measured value of mixed specimen (theoretical value) | Measured value of mixed specimen (actual measurement value) | Addition recovery rate (%) |
|---|---|---|---|---|---|
| N54 | 0.680 | 0.996 | 1.676 | 1.560 | 88.4 |
| N55 | 0.859 | 0.996 | 1.855 | 1.727 | 87.2 |
| N56 | 0.569 | 0.996 | 1.565 | 1.503 | 93.8 |
| N57 | 1.007 | 0.996 | 2.003 | 1.843 | 84.0 |
| N58 | 0.915 | 0.996 | 1.911 | 1.746 | 83.5 |
| N59 | 0.696 | 0.996 | 1.692 | 1.569 | 87.7 |
| N60 | 0.918 | 0.996 | 1.914 | 1.746 | 83.2 |
| N61 | 0.594 | 0.996 | 1.590 | 1.615 | 102.6 |

TABLE 3

Capture antibody: antibody No. 30, detection antibody: antibody No. 37

| Serum specimen | Measured value of diluted specimen | Measured value of standard substance | Measured value of mixed specimen (theoretical value) | Measured value of mixed specimen (actual measurement value) | Addition recovery rate (%) |
|---|---|---|---|---|---|
| N54 | 0.422 | 0.987 | 1.409 | 1.245 | 83.4 |
| N55 | 0.553 | 0.987 | 1.540 | 1.334 | 79.2 |
| N56 | 0.391 | 0.987 | 1.378 | 1.239 | 86.0 |
| N57 | 0.689 | 0.987 | 1.676 | 1.470 | 79.2 |
| N58 | 0.592 | 0.987 | 1.579 | 1.409 | 82.8 |
| N59 | 0.480 | 0.987 | 1.467 | 1.322 | 85.4 |
| N60 | 0.590 | 0.987 | 1.577 | 1.490 | 91.2 |
| N61 | 0.416 | 0.987 | 1.403 | 1.316 | 91.2 |

As shown in Tables 1 to 3, it was confirmed that in any of ELISAs of ELISA using antibody No. 30 as a capture antibody and HRP-labeled antibody No. 33 as a labeled detection antibody, ELISA using antibody No. 30 as a capture antibody and HRP-labeled antibody No. 36 as a labeled detection antibody, and ELISA using antibody No. 30 as a capture antibody and HRP-labeled antibody No. 37 as a labeled detection antibody, the addition recovery rate was equal to or more than 79%, and in any of ELISAs, APOA4 in the specimen could be accurately measured.

Example 10: Correlation Between the Measured Value of Human Serum APOA4 by ELISA and the Measured Value by LC/MS Using 5 specimens of healthy human serum, APOA4 in the serum was measured in the same manner as in Example 6. In addition, APOA4 of the same specimen was quantified by a selective reaction monitoring method using LC/MS (Liquid Chromatography/Mass Spectrometry), and the correlation between the measured value of human serum APOA4 by ELISA and the measured value of human serum APOA4 by LC/MS was examined. The result is shown in FIG. 5.

Figure 5:
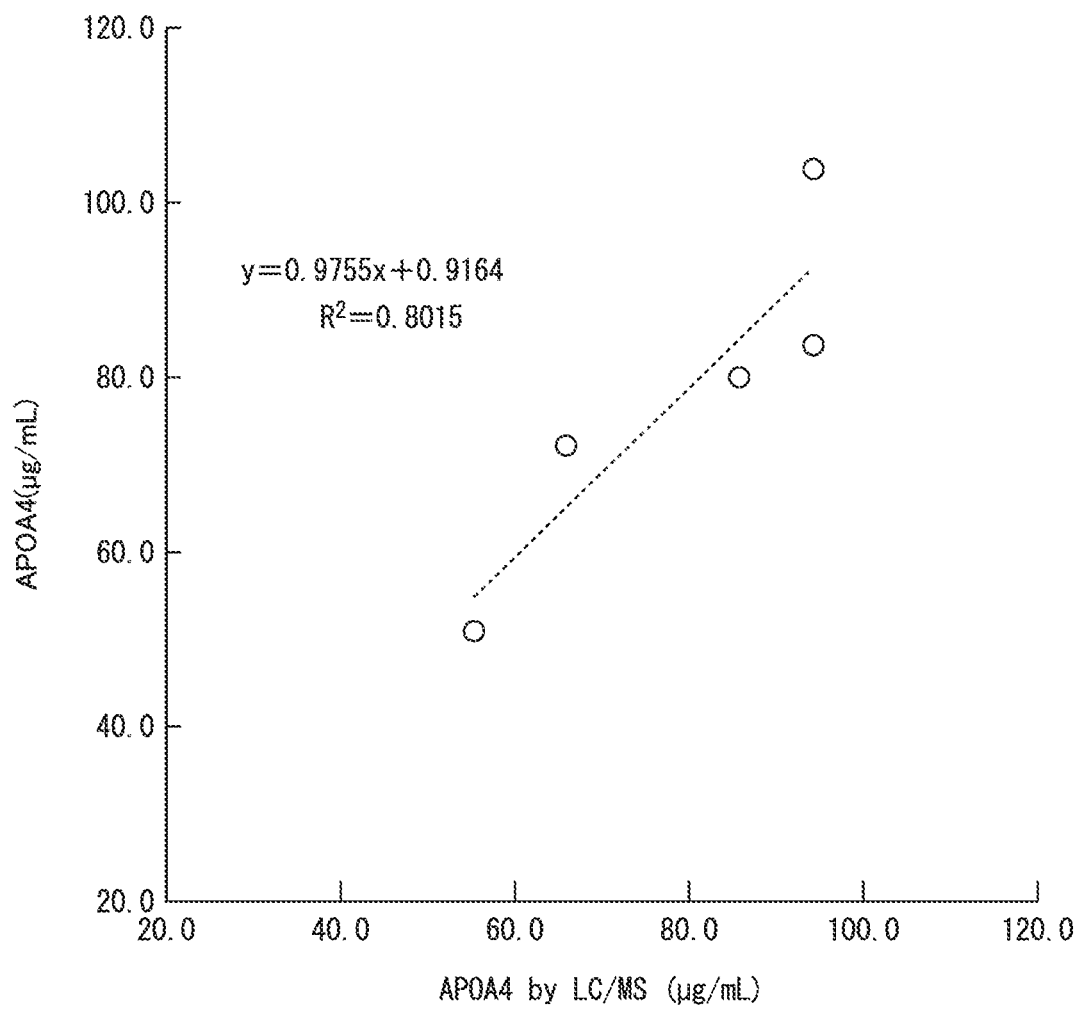
FIG. 5 is a figure representing the correlation between a measurement value of APOA4 in human serum by ELISA using the anti-APOA4 monoclonal antibody of the present invention and a measurement value of APOA4 in human serum by LC/MS.

As shown in FIG. 5, the correlation coefficient was 0.8015, and a favorable correlation was observed between the measured value of APOA4 by ELISA of the present invention and the measured value by LC/MS.

In addition, since the inclination of the correlation coefficient regression equation is close to 1 and is a straight line substantially passing through the original point, it was confirmed that the measured value by ELISA and the measured value by LC/MS were similar as absolute values.

From these results, it was confirmed that the ELISA of the present invention can accurately measure APOA4 in a specimen.

Example 11: Analysis of Amino Acid Sequences of Variable Regions of Antibody No. 30, Antibody No. 33, Antibody No. 36, and Antibody No. 37

The signal sequence of the heavy chain and the light chain of each of antibody No. 30, antibody No. 33, antibody No. 36, and antibody No. 37, and the DNA sequence encoding the variable region were amplified by a 5'-RACE (5'-rapid amplification of cDNA ends) method as follows.

From the hybridoma obtained in Example 3, total RNA was prepared using RNeasy Mini Kit (manufactured by QIAGEN) and processed with DNase (RNase free DNase set, manufactured by QIAGEN). A double-strand cDNA was prepared from the obtained total RNA using SMARTTER-™RACE 5'/3' kit (manufactured by TAKARA). From the prepared cDNA, the signal sequence of the antibody and the gene sequence encoding a variable region were amplified using a 5' forward primer (Universal Primer Mix) and a 3' reverse primer (a reverse primer consisting of a base sequence represented by SEQ ID NO: 35 was used for amplification of the mouse IgG heavy chain, and a reverse primer consisting of a base sequence represented by SEQ ID NO: 36 was used for amplification of the mouse Igκ light chain) attached to the kit. The amplified gene sequence was inserted into a pCR2.1 vector (manufactured by Invitrogen/Life Technologies). Gene sequences of antibody No. 30, antibody No. 33, antibody No. 36, and antibody No. 37 were analyzed using ABI3130XL. By the analysis, a gene sequence encoding a variable region including a signal sequence and a CDR sequence of each antibody was determined, and was converted to an amino acid sequence by gene analysis software Genetyx (Genetyx Corporation).

As a result, amino acid sequences of the heavy chain variable region and the light chain variable region of each antibody were determined as follows.
(1) Antibody No. 30
Heavy chain variable region: amino acid sequence represented by SEQ ID NO: 27
Light chain variable region: amino acid sequence represented by SEQ ID NO: 31
(2) Antibody No. 33
Heavy chain variable region: amino acid sequence represented by SEQ ID NO: 28
Light chain variable region: amino acid sequence represented by SEQ ID NO: 32
(3) Antibody No. 36
Heavy chain variable region: amino acid sequence represented by SEQ ID NO: 29
Light chain variable region: amino acid sequence represented by SEQ ID NO: 33
(4) Antibody No. 37
Heavy chain variable region: amino acid sequence represented by SEQ ID NO: 30
Light chain variable region: amino acid sequence represented by SEQ ID NO: 34

Example 12: Analysis of Amino Acid Sequences of CDRs of Antibody No. 30, Antibody No. 33, Antibody No. 36, and Antibody No. 37

The CDRs of antibody No. 30, antibody No. 33, antibody No. 36, and antibody No. 37 were determined by numbering amino acid sequences of respective antibodies using Abysis software (license from UCL) according to the Kabat numbering system, and by Kabat definition for identification of CDR based on the numbers.
The amino acid sequences of CDRs of antibody No. 30, antibody No. 33, antibody No. 36, and antibody No. 37 were determined as follows.
(1) Antibody No. 30
Heavy chain CDR1: amino acid sequence represented by SEQ ID NO: 3
Heavy chain CDR2: amino acid sequence represented by SEQ ID NO: 4
Heavy chain CDR3: amino acid sequence represented by SEQ ID NO: 5
Light chain CDR1: amino acid sequence represented by SEQ ID NO: 15
Light chain CDR2: amino acid sequence represented by SEQ ID NO: 16
Light chain CDR3: amino acid sequence represented by SEQ ID NO: 17
(2) Antibody No. 33
Heavy chain CDR1: amino acid sequence represented by SEQ ID NO: 6
Heavy chain CDR2: amino acid sequence represented by SEQ ID NO: 7
Heavy chain CDR3: amino acid sequence represented by SEQ ID NO: 8
Light chain CDR1: amino acid sequence represented by SEQ ID NO: 18
Light chain CDR2: amino acid sequence represented by SEQ ID NO: 19
Light chain CDR3: amino acid sequence represented by SEQ ID NO: 20
(3) Antibody No. 36
Heavy chain CDR1: amino acid sequence represented by SEQ ID NO: 9
Heavy chain CDR2: amino acid sequence represented by SEQ ID NO: 10
Heavy chain CDR3: amino acid sequence represented by SEQ ID NO: 11
Light chain CDR1: amino acid sequence represented by SEQ ID NO: 21
Light chain CDR2: amino acid sequence represented by SEQ ID NO: 22
Light chain CDR3: amino acid sequence represented by SEQ ID NO: 23
(4) Antibody No. 37
Heavy chain CDR1: amino acid sequence represented by SEQ ID NO: 12
Heavy chain CDR2: amino acid sequence represented by SEQ ID NO: 13
Heavy chain CDR3: amino acid sequence represented by SEQ ID NO: 14
Light chain CDR1: amino acid sequence represented by SEQ ID NO: 24
Light chain CDR2: amino acid sequence represented by SEQ ID NO: 25
Light chain CDR3: amino acid sequence represented by SEQ ID NO: 26

Example 13: Isotypes of Antibody No. 30, Antibody No. 33, Antibody No. 36, and Antibody No. 37

The hybridoma clone obtained in Example 2(3) was cultured, and antibody No. 30, antibody No. 33, antibody No. 36, and antibody No. 37 were purified from the culture supernatant using Protein A (manufactured by GE Healthcare). The isotype was determined using a monoclonal antibody isotyping kit (manufactured by BD Biosciences). As a result, the isotype of antibody No. 30 was IgG2b, κ. In addition, the isotypes of antibody No. 33, antibody No. 36, and antibody No. 37 were IgG1, κ.

Example 14: Epitope Map by HDX-MS of Antibody No. 30 and Antibody No. 33

A solution in which about 10 μM of antibody No. 30 or antibody No. 33 were added to 10 μM of rhAPOA4-His and rhAPOA4-His and mixed therewith was diluted 20-fold with a PBS deuterium solution to start a deuteration reaction. As a control, a PBS solution was used.
After 1 minute, 10 minutes, 60 minutes, and 240 minutes at 23° C., an equivalent amount of 500 mM TCEP solution (pH 3 or less) containing cooled 2M guanidine hydrochloride was added to stop the reaction. After digesting the reaction solution with a pepsin column, peptide was separated and eluted by reversed-phase liquid chromatography using a C18 column, and LC-MS/MS measurement was performed with a mass spectrometer.
Each peptide derived from rhAPOA4-His was identified from the mass data, and the amount of deuterium exchange at each reaction time was calculated from the mass value. The peptide in which the amount of deuterium exchange was changed depending on the presence or absence of the antibody was extracted as an estimated epitope region. As a result, remarkable suppression of deuteration was observed in peptides including an amino acid sequence from an 89th to a 110th amino acid and an amino acid sequence from a 200th to a 224th amino acid of the amino acid sequence represented by SEQ ID NO: 2, for antibody No. 30, and in peptides including an amino acid sequence from a 122nd to a 144th amino acid, an amino acid sequence from a 156th to a 177th amino acid, and an amino acid sequence from a 242nd to a 252nd amino acid of the amino acid sequence represented by SEQ ID NO: 2, for antibody No. 33.

From the results, the epitopes of antibody No. 30 were identified as an amino acid sequence from an 89th to a 110th amino acid and an amino acid sequence from a 200th to a 224th amino acid of the amino acid sequence represented by SEQ ID NO: 2. In addition, the epitopes of antibody No. 33 were identified as an amino acid sequence from a 122nd to a 144th amino acid, an amino acid sequence from a 156th to a 177th amino acid, and an amino acid sequence from a 242nd to a 252nd amino acid of the amino acid sequence represented by SEQ ID NO: 2.

By mapping the identified peptides to the X-ray crystal structure of the reported APOA4 dimer, it was clarified that the epitope peptides of antibody No. 30 and antibody No. 33 constitute one epitope region in the three-dimensional structure, and the epitope sites are different in antibody No. 30 and antibody No. 33.

INDUSTRIAL APPLICABILITY

According to the present invention, an anti-APOA4 monoclonal antibody or an antibody fragment thereof capable of accurately measuring APOA4 in a specimen, a measurement method for immunologically measuring APOA4 using the monoclonal antibody or the antibody fragment thereof, and a kit for measuring APOA4 containing the monoclonal antibody or the antibody fragment thereof can be provided.

The invention claimed is:

1. An anti-APOA4 monoclonal antibody, or an antibody fragment thereof, that specifically binds to human APOA4, comprising:
   a heavy chain complementarity determining region (CDR) 1 comprising the amino acid sequence set forth in SEQ ID NO: 3;
   a heavy chain CDR2 comprising the amino acid sequence set forth in SEQ ID NO: 4;
   a heavy chain CDR3 comprising the amino acid sequence set forth in SEQ ID NO: 5;
   a light chain CDR1 comprising the amino acid sequence set forth in SEQ ID NO: 15;
   a light chain CDR2 comprising the amino acid sequence set forth in SEQ ID NO: 16; and
   a light chain CDR3 comprising the amino acid sequence set forth in SEQ ID NO: 17.

2. The anti-APOA4 monoclonal antibody or the antibody fragment thereof according to claim 1, comprising:
   a heavy chain variable region comprising the amino acid sequence set forth in SEQ ID NO: 27; and
   a light chain variable region comprising the amino acid sequence set forth in SEQ ID NO: 31.

3. The anti-APOA4 monoclonal antibody or the antibody fragment thereof according to claim 1, which binds to a monomer and a dimer of human APOA4.

4. An anti-APOA4 monoclonal antibody, or an antibody fragment thereof, that specifically binds to human APOA4, comprising:
   a heavy chain CDR1 comprising the amino acid sequence set forth in SEQ ID NO: 6;
   a heavy chain CDR2 comprising the amino acid sequence set forth in SEQ ID NO: 7;

a heavy chain CDR3 comprising the amino acid sequence set forth in SEQ ID NO: 8;
a light chain CDR1 comprising the amino acid sequence set forth in SEQ ID NO: 18;
a light chain CDR2 comprising the amino acid sequence set forth in SEQ ID NO: 19; and
a light chain CDR3 comprising the amino acid sequence set forth in SEQ ID NO: 20.

5. The anti-APOA4 monoclonal antibody or the antibody fragment thereof according to claim 4, comprising:
a heavy chain variable region comprising the amino acid sequence set forth in SEQ ID NO: 28; and
a light chain variable region comprising the amino acid sequence set forth in SEQ ID NO: 32.

6. The anti-APOA4 monoclonal antibody or the antibody fragment thereof according to claim 4, which binds to a monomer and a dimer of human APOA4.

7. An anti-APOA4 monoclonal antibody, or an antibody fragment thereof, that specifically binds to human APOA4, comprising:
a heavy chain CDR1 comprising the amino acid sequence set forth in SEQ ID NO: 9;
a heavy chain CDR2 comprising the amino acid sequence set forth in SEQ ID NO: 10;
a heavy chain CDR3 comprising the amino acid sequence set forth in SEQ ID NO: 11;
a light chain CDR1 comprising the amino acid sequence set forth in SEQ ID NO: 21;
a light chain CDR2 comprising the amino acid sequence set forth in SEQ ID NO: 22; and
a light chain CDR3 comprising the amino acid sequence set forth in SEQ ID NO: 23.

8. The anti-APOA4 monoclonal antibody or the antibody fragment thereof according to claim 7, comprising:
a heavy chain variable region comprising the amino acid sequence set forth in SEQ ID NO: 29; and
a light chain variable region comprising the amino acid sequence set forth in SEQ ID NO: 33.

9. The anti-APOA4 monoclonal antibody or the antibody fragment thereof according to claim 7, which binds to a monomer and a dimer of human APOA4.

10. An anti-APOA4 monoclonal antibody, or an antibody fragment thereof, that specifically binds to human APOA4, comprising:
a heavy chain CDR1 comprising the amino acid sequence set forth in SEQ ID NO: 12;
a heavy chain CDR2 comprising the amino acid sequence set forth in SEQ ID NO: 13;
a heavy chain CDR3 comprising the amino acid sequence set forth in SEQ ID NO: 14;
a light chain CDR1 comprising the amino acid sequence set forth in SEQ ID NO: 24;
a light chain CDR2 comprising the amino acid sequence set forth in SEQ ID NO: 25; and
a light chain CDR3 comprising the amino acid sequence set forth in SEQ ID NO: 26.

11. The anti-APOA4 monoclonal antibody or the antibody fragment thereof according to claim 10, comprising:
a heavy chain variable region comprising the amino acid sequence set forth in SEQ ID NO: 30; and
a light chain variable region comprising the amino acid sequence set forth in SEQ ID NO: 34.

12. The anti-APOA4 monoclonal antibody or the antibody fragment thereof according to claim 10, which binds to a monomer and a dimer of human APOA4.

13. A measurement method for immunologically measuring APOA4 in a specimen, the method comprising:

binding human APOA4 in the specimen to a capture antibody which specifically binds to the human APOA4,
adding a labeled detection antibody in which a label is bound to a detection antibody that specifically binds to the APOA4 to form an immune complex consisting of the human APOA4, the capture antibody, and the labeled detection antibody, and
measuring an amount of label in the formed immune complex,
wherein the capture antibody and the detection antibody are selected from the anti-APOA4 monoclonal antibody or the antibody fragment thereof according to any one of claims 1, 4, 7, and 10, and the capture antibody and the detection antibody are different from each other.

14. The measurement method according to claim 13, wherein the capture antibody is the anti-APOA4 monoclonal antibody or the antibody fragment thereof according to claim 1.

15. The measurement method according to claim 13, wherein the detection antibody is the anti-APOA4 monoclonal antibody or the antibody fragment thereof according to claim 4.

16. The measurement method according to claim 13, wherein the capture antibody is the anti-APOA4 monoclonal antibody or the antibody fragment thereof according to claim 1, and the detection antibody is the anti-APOA4 monoclonal antibody or the antibody fragment thereof according to claim 4.

17. The measurement method according to claim 13, wherein the capture antibody is the anti-APOA4 monoclonal antibody or the antibody fragment thereof according to claim 1, and the detection antibody is the anti-APOA4 monoclonal antibody or the antibody fragment thereof according to claim 7.

18. The measurement method according to claim 13, wherein the capture antibody is the anti-APOA4 monoclonal antibody or the antibody fragment thereof according to claim 1, and the detection antibody is the anti-APOA4 monoclonal antibody or the antibody fragment thereof according to claim 10.

19. The measurement method according to claim 13, wherein the label is an enzyme.

20. The measurement method according to claim 13, wherein the capture antibody is immobilized on a solid support.

21. The measurement method according to claim 13, wherein the specimen is selected from the group consisting of blood, a lymphatic fluid, a tissue fluid, and a body cavity fluid.

22. The measurement method according to claim 13, wherein the specimen is blood.

23. The measurement method according to claim 22, wherein the blood is whole blood, plasma, or serum.

24. A kit for measuring human APOA4 in a specimen, comprising:
a capture antibody that specifically binds to human APOA4; and
a labeled detection antibody in which a label is bound to a detection antibody that specifically binds to the human APOA4,
wherein the capture antibody and the detection antibody are selected from the anti-APOA4 monoclonal antibody or the antibody fragment thereof according to any one of claims 1, 4, 7, and 10, and the capture antibody and the detection antibody are different from each other.

25. The kit according to claim 24, wherein the capture antibody is the anti-APOA4 monoclonal antibody or the antibody fragment thereof according to claim 1.

26. The kit according to claim 24, wherein the detection antibody is the anti-APOA4 monoclonal antibody or the antibody fragment thereof according to claim 4.

27. The kit according to claim 24, wherein the capture antibody is the anti-APOA4 monoclonal antibody or the antibody fragment thereof according to claim 1, and the detection antibody is the anti-APOA4 monoclonal antibody or the antibody fragment thereof according to claim 4.

28. The kit according to claim 24, wherein the capture antibody is the anti-APOA4 monoclonal antibody or the antibody fragment thereof according to claim 1, and the detection antibody is the anti-APOA4 monoclonal antibody or the antibody fragment thereof according to claim 7.

29. The kit according to claim 24, wherein the capture antibody is the anti-APOA4 monoclonal antibody or the antibody fragment thereof according to claim 1, and the detection antibody is the anti-APOA4 monoclonal antibody or the antibody fragment thereof according to claim 10.

30. The kit according to claim 24, wherein the label is an enzyme.

31. The kit according to claim 24, wherein the capture antibody is immobilized on a solid support.

* * * * *